(12) United States Patent
Park et al.

(10) Patent No.: US 9,949,928 B2
(45) Date of Patent: Apr. 24, 2018

(54) BIODEGRADABLE COPOLYMERS, SYSTEMS INCLUDING THE COPOLYMERS, AND METHODS OF FORMING AND USING SAME

(71) Applicants: Daewon Park, Englewood, CO (US); Malik Kahook, Denver, CO (US); Amin Famili, Denver, CO (US)

(72) Inventors: Daewon Park, Englewood, CO (US); Malik Kahook, Denver, CO (US); Amin Famili, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 14/888,678

(22) PCT Filed: May 1, 2014

(86) PCT No.: PCT/US2014/036446
§ 371 (c)(1),
(2) Date: Nov. 2, 2015

(87) PCT Pub. No.: WO2014/179615
PCT Pub. Date: Nov. 6, 2014

(65) Prior Publication Data
US 2016/0051469 A1    Feb. 25, 2016

Related U.S. Application Data

(60) Provisional application No. 61/818,388, filed on May 1, 2013.

(51) Int. Cl.
| A61K 9/107 | (2006.01) |
| A61K 9/00 | (2006.01) |
| A61K 47/34 | (2017.01) |

(52) U.S. Cl.
CPC .......... *A61K 9/1075* (2013.01); *A61K 9/0024* (2013.01); *A61K 9/0051* (2013.01); *A61K 47/34* (2013.01)

(58) Field of Classification Search
None
See application file for complete search history.

(56) References Cited

U.S. PATENT DOCUMENTS

| 5,702,717 A | 12/1997 | Cha et al. |
| 6,100,338 A | 8/2000 | Akashi et al. |
| 6,469,132 B1 * | 10/2002 | Eisenberg ............ C08G 63/664 528/354 |
| 6,486,213 B1 * | 11/2002 | Chen ..................... A61K 8/91 514/772.1 |
| 6,599,519 B1 * | 7/2003 | Seo ....................... A61K 9/1075 424/184.1 |
| 6,841,617 B2 | 1/2005 | Jeong et al. |
| 8,309,623 B2 | 11/2012 | Yu et al. |
| 2001/0014354 A1 * | 8/2001 | Yokoyama ........... A61K 9/1075 424/490 |
| 2005/0089545 A1 | 4/2005 | Kuwano et al. |
| 2008/0193536 A1 * | 8/2008 | Khademhosseini . A61K 35/545 424/486 |
| 2009/0098044 A1 * | 4/2009 | Kong .................... A61K 9/107 424/1.29 |
| 2010/0015195 A1 * | 1/2010 | Jain ....................... A61K 9/0024 424/422 |
| 2011/0182813 A1 | 7/2011 | Heller et al. |

FOREIGN PATENT DOCUMENTS

| WO | 2010088548 A1 | 8/2010 |
| WO | 2011109732 A2 | 9/2011 |
| WO | WO 2011109732 A2 * | 9/2011 ........... A61K 9/0024 |

OTHER PUBLICATIONS

Chen et al. Macromolecular Rapid Communications 1995 16:175-182.*
Durand et al. Polymer 1999 40:4941-4951.*
Park et al. Biomaterials 2011 32:777-786.*
Geng et al. Nanoscale Research Letters 2011 6:312-319.*
Trivedi et al. Nanomedicine (London) 2010 5(3):485-505; repaginated as 1-31.*
Kim et al. Journal of Controlled Release 1998 51:13-22.*
Shuai et al. Journal of Controlled Release 2004 98:415-426.*
Chung et al. Biomacromolecules 2002 3:511-516.*
Ying et al. Journal of Membrane Science 2004 243:253-262.*
Schacht et al. Journal of Controlled Release 2006 116:219-225.*
Gohy et al. Advances in Polymer Science 2005 190: 65-136; pp. 65, 68-69 are provided.*
Nardin et al. Langmuir 2000 16(3):1035-1041.*
Berger et al. International Journal of Pharmaceutics 2001 223:55-68.*
Park, D. et al., "A functionalizable reverse thermal gel based on a polyurethane/PEG block copolymer," National Institutes of Health, Biomaterials, Jan. 2011, pp. 1-23, 32(3): 777-786.
WIPO; International Search Report dated Apr. 3, 2015 in corresponding International App. No. PCT/US14/36446.

(Continued)

*Primary Examiner* — Robert A Wax
*Assistant Examiner* — Caralynne E Helm
(74) *Attorney, Agent, or Firm* — Snell & Wilmer L.L.P.

(57) ABSTRACT

Therapeutic agent delivery systems, which include a thermally-sensitive copolymer and optionally a therapeutic agent, are disclosed. The copolymer is water soluble and biodegradable and, in accordance with exemplary embodiments, includes hydrophobic and hydrophilic portions. The systems may include supplemental compounds, such as polymeric nanoparticles, micelle compounds, or a combination thereof, to further provide sustained release of the therapeutic agent.

12 Claims, 22 Drawing Sheets

(56) References Cited

OTHER PUBLICATIONS

WIPO; Written Opinion dated Apr. 3, 2015 in corresponding International App. No. PCT/US14/36446.
WIPO; International Preliminary Report on Patentability dated Nov. 12, 2015 in corresponding International App. No. PCT/US14/36446.

* cited by examiner

Lower critical solution temperature (LCST) measurements as determined by UV-visible spectroscopic measurements at 480 nm. RTG A formulation is PSHU-PNIPAAm graft copolymer with a 100% conjugation ratio and RTG B formulation is PSHU-PNIPAAm graft copolymer with a 25% conjugation ratio.

Temperature dependent-behavior of G', the elastic/solid component of the modulus, as determined by rheological analysis. The phase transition temperature can be controlled by adjusting the concentration of RTG in phosphate-buffered saline (pH 7.4). Formulation is PSHU-PNIPAAm with a 25% conjugation ratio.

Temperature dependent-behavior of G", the viscous/liquid component of the modulus, as determined by rheological analysis. The phase transition temperature can be controlled by adjusting the concentration of RTG in phosphate-buffered saline (ph 7.4). Formulation is PSHU-PNIPAAm with a 25% conjugation ratio.

Release of triamcinolone acetonide (10 wt% loading) from micelles of two different molecular weights: low MW (Mw = 48 kDa) and high MW (Mw = 93 kDa). Release medium was PBS, pH 7.4. Formulation is PEG-PHS-PEG triblock copolymer.

Release of triamcinolone acetonide (5 or 10 wt% loading) from RTG of two different concentrations: 5 wt% and 10 wt%. Release medium was PBS, pH 7.4 and RTG formulation was PSHU-PNIPAAm with a 25% conjugation ratio.

Cytotoxicity study of PSHU-PNIPAAm RTG as conducted per ISO 10993-5. Extractions of the RTG copolymer were non-cytotoxic against ARPE-19 cell cultures as assayed by MTT for metabolic activity.

Synthesized HO-PNIPAAm-COOH molecular weight followed closely to theoretically calculated values and was dependent on the molar fraction of CTA employed.

$^1$H NMR spectroscopy confirmed the structure of PSHU. *Inset:* The proton peak associated with Boc protective groups at 1.34 ppm in the base polymer (*) was absent after the complete deprotection routine (**).

FT-IR analyses of the base polymers and the final copolymer confirmed conjugation in PSHU-NIPAAm through the peaks at 1650-1700 cm$^{-1}$ (A, amide C=O stretch). 950 cm$^{-1}$ (B, carboxyl O-H bend) and 798 cm$^{-1}$ (C, primary amine N-H wag).

$^1$H NMR (500 MHz, CDCl$_3$) analysis of the PEG-PHS-PEG copolymer, illustrating the hydrophobic PHS block (N-Boc serine): B, G, H and J and HDI: A, C, D and I) and successful capping by mPEG (E and F). Peak assignments were corroborated by NMR modeling (Advanced Chemistry Development).

BIODEGRADABLE COPOLYMERS, SYSTEMS INCLUDING THE COPOLYMERS, AND METHODS OF FORMING AND USING SAME

CROSS REFERENCE TO RELATED APPLICATIONS

This application is the national stage entry of International Application No. PCT/US14/036446, entitled BIODEGRADABLE COPOLYMERS, SYSTEMS INCLUDING THE COPOLYMERS, AND METHODS OF FORMING AND USING SAME, filed on May 1, 2014, and claims the benefit of U.S. Provisional Application Ser. No. 61/818,388, filed May 1, 2013, entitled BIODEGRADABLE COPOLYMERS, SYSTEMS INCLUDING THE COPOLYMERS, AND METHODS OF FORMING AND USING SAME, the contents of which are hereby incorporated herein by reference.

FIELD OF DISCLOSURE

The present disclosure generally relates to therapeutic agent delivery systems and components thereof. More particularly, various examples of the disclosure relate to therapeutic agent delivery systems that include a copolymer that undergoes a phase transition (e.g., from a liquid to a gel, formation of micelles, or the like) with temperature and optionally a therapeutic agent, to components of the systems, to devices including the systems, and to methods of forming and using the systems.

BACKGROUND OF THE DISCLOSURE

A major obstacle in designing an effective ocular drug delivery system is the anatomical challenge presented by the eye. Both in access and available space, the eye is unlike any other organ due to its isolation and compactness. Because of these limitations, ocular drug delivery systems will desirably include, for example, 1) minimally-invasive deployment, 2) sustained drug release on the scale of several months to years (including release of formulation-challenging drugs, such as those with limited aqueous solubility), 3) extremely high biocompatibility, and 4) biodegradation on a time scale similar to release of the entire drug payload. Unfortunately, typical delivery systems generally do not meet one or more of these criteria.

Reverse thermal gels (RTGs) have been proposed to address some of these desired criteria. However, typical reverse thermal gels generally have poor drug-eluting characteristics, which are generally due to high water content of the gels. Although the high level of water contributes to a biocompatibility of the gel, the high water content (typically greater than 90%), causes the gels to suffer from an inability to hinder rapid diffusion of a drug out of the system or gel. As a result, such systems generally have a release period that is at most on the order of days to a couple of weeks. In addition, typical RTG systems are relatively unstable, because the systems are loaded with drugs at concentrations above a solubility level of the drug in order to be clinically relevant.

Accordingly, improved methods, systems, and devices for providing sustained therapeutic agent delivery are desired.

SUMMARY OF THE DISCLOSURE

The present disclosure generally relates to therapeutic agent delivery systems, which include a water-soluble thermally-sensitive copolymer and optionally one or more therapeutic agents. While the ways in which the compositions and systems described herein address the various drawbacks of known compositions and systems, in general, the compositions and systems described herein may be configured to provide sustained release of the therapeutic agent(s) over a prolonged period of time.

In accordance with various exemplary embodiments of the disclosure, a system includes a reverse thermal gel (RTG), which is an aqueous polymer solution that reversibly transitions from a liquid to a physical gel as a temperature of the system is increased beyond a pre-determined temperature and from a gel back to a liquid as the temperature of the system falls below a pre-determined temperature. The RTG can include thermally-sensitive segments and/or hydrophobic and hydrophilic segments (prior to a transition from liquid to gel). In accordance with exemplary aspects of these embodiments, a system further includes one or more supplemental therapeutic agent delivery systems (or supplemental compounds), such as one or more compounds selected from the group consisting of polymeric or non-organic nanoparticle systems, one or more polymeric or surfactant-based micelle systems, one or more liposome systems, or a combination thereof, and optionally one or more therapeutic agents. The one or more supplemental compounds may be distributed within the reverse thermal gel. The combination of the RTG (e.g., a copolymer) and the one or more supplemental compounds provides a controlling mechanism for release of the therapeutic agent, allowing for its sustained delivery over an extended period of time—e.g., over a period of greater than 3 months, 3-12 months, 3-6 months, 4-6 months, or greater than 12 months. In accordance with exemplary aspects of these embodiments, the one or more supplemental compounds improve the long-term release behavior of the system, while the RTG provides a scaffold for the retention of the one or more supplemental compounds. In accordance with further exemplary aspects of these embodiments, the reverse thermal gel comprises or is a grafted copolymer, wherein the backbone polymer may be selected from, for example, the group consisting of poly[hexamethylene-alt-(serinol; urea)] (PHSU)—also referred to herein as poly(serinol hexamethylene urea) (PSHU), polyurethane, poly(ester urethane), polyamide, polycarbonate, polyurea, polyacrylate, polyester, polystyrene or polyvinyl compounds, and the graft polymer may be selected from, for example, the group consisting of poly(N-isopropylacrylamide) (PNIPAAm), hydroxypropylcellulose, poly(vinylcaprolactame), polyvinyl methyl ether, polyethylene oxide, polyvinylmethylether, polyhydroxyethylmethacrylate, poly(N-acryloylglycinamide), ureido-functionalized polymer, acrylamide-based copolymer, or acrylonitrile-based copolymer compounds. Alternatively, the copolymer may be a liner copolymer including, for example, PHSU or esterified versions thereof (ePHSU) and PNIPAAm. In accordance with various aspects of these embodiments, the RTG is configured with a segment (e.g., a grafted segment) that can be easily severed from a portion (e.g., the backbone) of the copolymer. For example, in accordance with some examples, the segment (e.g., PNIPAAm) can be configured to be easily severed in the presence of an acid, enzyme(s), or other degradation agent(s). The molecule/segment can have a lower critical solution temperature above a body temperature, and the copolymer including a polymer and the molecule can have a critical solution temperature that is below the body temperature. In accordance with further aspects of these embodiments, the one or more supplemental compounds include micelle compounds that include an AB diblock, ABA triblock and/or a graft copolymer, wherein A is a hydrophilic polymer selected from, for example, the group consisting of polyethylene glycol (PEG), polyether, polyacrylamide or poly(vinyl alcohol) compounds, and B is a hydrophobic polymer selected from, for example, the group consisting of poly(hexamethylene-alt-serinol) (PHS), polyurethane, poly(ester urethane), polyamide, polycarbonate, polyurea, polyacrylate, polyester, polystyrene or polyvinyl compounds. In the case of a graft copolymer, the backbone polymer may include any of the hydrophobic polymers noted above and the graft polymer may be any of the hydrophilic polymers noted above. A chain length of the hydrophilic polymer may range from about 500 to about 800 or about 400 to about 1000 and a chain length of the hydrophobic polymer may range from about 30000 to about 100000 or about 10000 to about 200000. In accordance with yet further aspects, the therapeutic agent delivery system includes a therapeutic agent selected from the group consisting of one or more drugs, one or more peptides, one or more cytokines, one or more growth factors, one or more proteins, or any combination thereof.

In accordance with further exemplary embodiments of the disclosure, a therapeutic agent delivery system includes a water-soluble, biodegradable copolymer comprising an ABA triblock copolymer, an AB diblock copolymer, a graft copolymer or a combination thereof, wherein A is selected from the group consisting of polyethylene glycol and polyNIPAAm and B is selected from the group consisting of polycarbonate, polyamide and polyurea; and optionally a first therapeutic agent mixed with the water-soluble, biodegradable block copolymer.

In accordance with yet further exemplary embodiments, a therapeutic agent delivery system includes a water-soluble, biodegradable graft copolymer, wherein the backbone is a hydrophobic copolymer having a molecular weight between about 2000 and 50000 and the grafted polymer is a hydrophilic polymer having a molecular weight between about 2000 and 50000, and optionally a first therapeutic agent mixed with the water-soluble, biodegradable block copolymer. The hydrophobic and hydrophilic polymers may include any of the respective hydrophobic and hydrophilic polymers described herein in connection with a reverse thermal gel.

In accordance with yet further exemplary embodiments, a therapeutic agent delivery system includes a water-soluble, biodegradable graft copolymer, wherein the backbone is a hydrophobic copolymer containing an amino-substituted or N-substituted serinol in which the N is substituted with a protective group such that this protective group can be removed and optionally further conjugated with a therapeutic compound—e.g., without the system losing thermal gelling properties. In accordance with exemplary aspects of these embodiments, N may be substituted with hydrogen, a protective group, or an active agent. The hydrophobic copolymer and the graft copolymer may include, respectively, any of the hydrophobic polymers and hydrophilic polymers described herein with regard to a reverse thermal gel.

In accordance with additional embodiments of the disclosure, a therapeutic agent delivery system includes optionally one or more therapeutic agents and a water-soluble, biodegradable graft copolymer, where the backbone polymer may be selected from, for example, the group consisting of poly[hexamethylene-alt-(serinol; urea)] (PHSU), polyurethane, poly(ester urethane), polyamide, polycarbonate, polyurea, polyacrylate, polyester, polystyrene or polyvinyl compounds and the graft polymer may be selected from, for example, the group consisting of poly(N-isopropylacrylamide) (PNIPAAm), hydroxypropylcellulose, poly(vinylcaprolactame), polyvinyl methyl ether, polyethylene oxide, polyvinylmethylether, polyhydroxyethylmethacrylate, poly(N-acryloylglycinamide), ureido-functionalized polymer, acrylamide-based copolymer, or acrylonitrile-based copolymer compounds or a linear copolymer comprising, for example, esterified PHSU (ePHSU) and PNIPAAm. In accordance with various aspects of these embodiments, the system further includes one or more supplemental therapeutic agent delivery systems or supplemental compounds, such as one or more nanoparticles, one or more micelle structures, one or more liposome structures or a combination thereof, to obtain a desired release rate of the therapeutic agent(s). Exemplary micelle structures suitable for various aspects of these embodiments include an AB diblock, an ABA triblock, and/or a graft copolymer (wherein A is grafted to B), wherein A is a hydrophilic polymer selected from, for example, the group consisting of, for example, polyethylene glycol, polyether, polyacrylamide or poly(vinyl alcohol) compounds and B is a hydrophobic polymer selected from, for example, the group consisting of poly(hexamethylene-alt-serinol) (PHS) polyurethane, poly(ester urethane), polyamide, polycarbonate, polyurea, polyacrylate, polyester, polystyrene or polyvinyl compounds. A chain length of the hydrophilic polymer may range from about 500 to about 800 or about 400 to about 1000 and a chain length of the hydrophobic polymer may range from about 30000 to about 100000 or about 10000 to about 200000. In accordance with further exemplary aspects of these embodiments, a chain length of the hydrophobic polymer is greater (e.g., by about a factor of about 1.2 to about 6.0) relative to the chain length of the hydrophilic polymer.

In accordance with various embodiments of the disclosure, at or around room temperature (25° C.), a system is a liquid with relatively low viscosity (e.g., about 0.01-2 Pa·s), so as to allow the system to be injected through a small gauge needle (e.g., gauge 30 needle or higher). As the temperature of the system rises, the system forms either micelles (also referred to herein as micelle structures) and/or a gel (depending on, e.g., a polymer concentration), at or slightly below body temperature (37° C.) and has a viscosity of about 15-650 Ps·s at 37° C.

In accordance with further embodiments, a therapeutic agent with medium to high hydrophobicity is incorporated into a system in its liquid state by simple mixing. Additionally or alternatively, a therapeutic agent may be attached to nanoparticles and/or loaded into micelle structures as described herein. In accordance with the further embodiments, a therapeutic agent may be grafted onto a backbone polymer of a reverse thermal gel—in addition to or as alternative to other means of incorporating the therapeutic agent into a system.

In accordance with yet further embodiments of the disclosure, micelle structures suitable for, for example, use as a supplemental compound include an AB diblock, an ABA triblock, and/or a graft (A grafted to B) copolymer, wherein A is a hydrophilic polymer selected from, for example, the group consisting of, for example, polyethylene glycol, polyether, polyacrylamide or poly(vinyl alcohol) compounds and B is a hydrophobic polymer selected from, for example, the group consisting of poly(hexamethylene-alt-serinol) (PHS), poly(ester urethane), polyamide, polycarbonate, polyurea, polyacrylate, polyester, polystyrene or polyvinyl compounds. A chain length of the hydrophilic polymer may range from about 500 to about 800 or about 400 to about 1000 and a chain length of the hydrophobic polymer may range from about 30000 to about 100000 or about 10000 to about 200000. In accordance with further exemplary aspects of these embodiments, a chain length of the hydrophobic polymer is greater (e.g., by about 1.2 to about 6.0) relative to the chain length of the hydrophilic polymer.

In accordance with yet additional embodiments of the disclosure, a device includes one or more therapeutic drug delivery systems as described herein. The device may include a reservoir for the system and may additionally include a mechanism, such as nanopores, which may form part of the device, to further control the rate of release of the therapeutic agent(s) and/or system.

In accordance with yet additional exemplary embodiments of the disclosure, a method of forming a reverse thermal gel includes the steps of forming a reverse thermal gel polymer comprising a graft polymer having a backbone polymer selected from, for example, the group consisting of poly[hexamethylene-alt-(serinol; urea)] (PHSU), polyurethane, poly(ester urethane), polyamide, polycarbonate, polyurea, polyacrylate, polyester, polystyrene or polyvinyl compounds and a graft polymer selected from, for example, the group consisting of poly(N-isopropylacrylamide) (PNIPAAm), hydroxypropylcellulose, poly(vinylcaprolactame), polyvinyl methyl ether, polyethylene oxide, polyvinylmethylether, polyhydroxyethylmethacrylate, poly(N-acryloylglycinamide), ureido-functionalized polymer, acrylamide-based copolymer, or acrylonitrile-based copolymer compounds. In accordance with various aspects of these embodiments, the method further includes the steps of adding water to the reverse thermal gel polymer to form a gel.

In accordance with yet additional exemplary embodiments of the disclosure, a method of forming a reverse thermal gel includes the steps of forming a reverse thermal gel polymer comprising a linear copolymer polymer including ePHSU and PNIPAAm. In accordance with various aspects of these embodiments, the method further includes the steps of adding water to the reverse thermal gel polymer to form a gel.

In accordance with further exemplary embodiments of the disclosure, a method of forming a system includes a step of forming a reverse thermal gel and adding a therapeutic agent to the gel. In accordance with exemplary aspects of these embodiments, the method further includes adding a supplemental therapeutic agent delivery system, such as nanoparticles, micelle structures, and/or liposome systems to the reverse thermal gel. In accordance with exemplary aspects of these embodiments, the method includes loading the therapeutic agent into micelle structures—e.g., using direct dialysis, emulsification, and/or extrusion.

In accordance with yet additional embodiments of the disclosure, a method of treatment includes the step of injecting a therapeutic agent delivery system as described herein into a patient in need of treatment. The step of injecting may include injecting the therapeutic agent delivery system into an eye. In this case, the system may be delivered via an intravitreal injection. In accordance with various aspects of these embodiments, the therapeutic agent delivery system is delivered via injection into one or more of the periocular spaces. In accordance with further aspects, the therapeutic agent delivery system is delivered via injection at or near the optic nerve. In accordance with yet further aspects, the step of injecting includes injecting the therapeutic agent delivery system into an implanted device, which may be located within an eye.

BRIEF DESCRIPTION OF THE DRAWING FIGURES

A more complete understanding of the embodiments of the present disclosure may be derived by referring to the detailed description and claims when considered in connection with the following illustrative figures.

Figure 1:
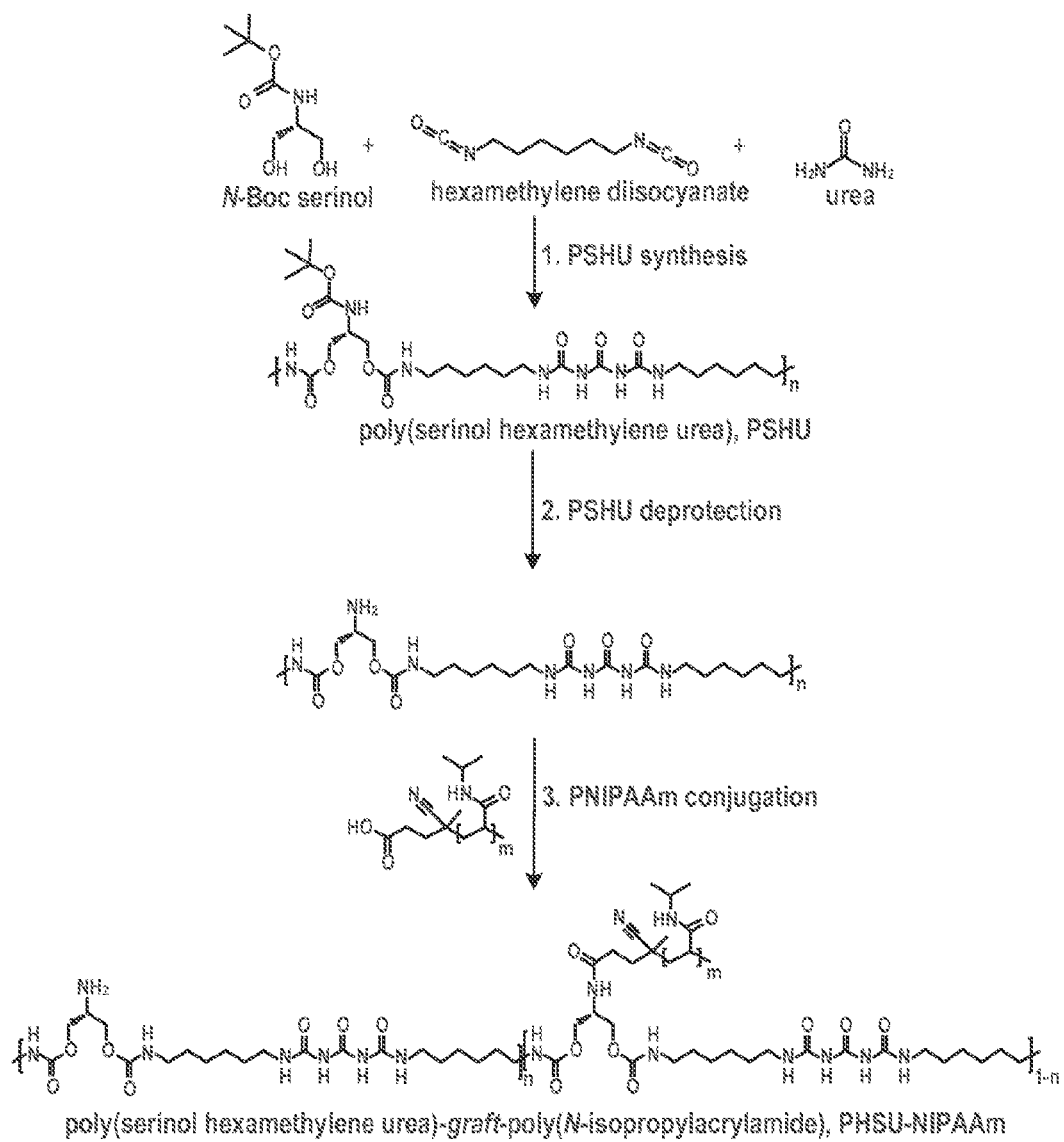
FIG. 1 illustrates a method of forming a graft copolymer: poly[hexamethylene-alt-(serinol; urea)]graft-poly(N-isopropylacrylamide) (PHSU-PNIPAAm) in accordance with exemplary embodiments of the disclosure.

A more complete understanding of the embodiments of the present disclosure may be derived by referring to the detailed description and claims when considered in connection with the following illustrative figures.

DETAILED DESCRIPTION OF PREFERRED EMBODIMENTS OF THE DISCLOSURE

The description of exemplary embodiments of the present disclosure provided below is merely exemplary and is intended for purposes of illustration only; the following description is not intended to limit the scope of the disclosure disclosed herein. Moreover, recitation of multiple embodiments having stated features is not intended to exclude other embodiments having additional features or other embodiments incorporating different combinations of the stated features.

The present disclosure provides improved systems, components thereof, devices, methods of using the systems and components (e.g., for delivery of a therapeutic agent), and methods of forming the systems and components thereof. The systems, devices, components, and methods described herein can be used for a variety of purposes and for the treatment of a variety of animals. The systems, devices, components, and methods are described below in connection with supplying a therapeutic agent to an eye (e.g., of a mammal, such as a human). Exemplary systems may be injected into, for example, an eye or other area of a patient in need of treatment, or into a device that resides in vivo or which is later implanted into the patient. However, unless otherwise stated, the disclosure is not so limited.

As set forth in more detail below, various systems in accordance with the present disclosure include a reverse thermal gel (RTG) to provide sustained release of one or more therapeutic agents. The RTG nature of the systems described herein allows for low viscosity injection of sustained-release systems into an eye, a device, or the like, with subsequent gelling of the system inside of the eye or the device. In the cases where a device is used, a secondary mechanism may be employed to further control of elution of the system. For example, the device may include nanopores or other means for limiting diffusion of the systems described herein.

By way of examples, exemplary reverse thermal gels have a viscosity of about 0.005 Pa·s to about 0.1 Pa·s at 20° C., so as to allow the system to be injected using, for example, a small gauge needle (e.g., 30 gauge, 32 gauge, or smaller). As the temperature of the system rises, the system forms micelles, a gel, or both at or slightly below body temperature (37° C.), the formation of which may depend polymer concentration and/or the system composition. By way of examples, the viscosity of the system at or slightly below 37° C. is about 15-650 Ps·s. An elastic modulus of the RTG may be from about 5 Pa to about 1000000 Pa at 37° C. A conjugation ratio of a copolymer, discussed in more detail below, may be selected to obtain a desired phase transition temperature (e.g., about 26° C. to about 36° C. or about 34° C.). As used herein, phase transition temperature means the lower critical solution temperature (LCST) at which the system goes from a solution to a non-solution or a gel. The viscosity values set forth herein are measured during the heating from 15° C. to 60° C. using rheometer. The measurement method is described in Park, D; Wu, W; Wang, Y. "A functionalizable reverse thermal gel based on a polyurethane/PEG block copolymer" *Biomaterials*, 32 (3), 777-86 (2011), the relevant portions of which are hereby incorporated herein by reference, to the extent such content does not conflict with this application. By changing viscosity and forming a gel upon reaching near body temperature, the delivery mechanism allows the system to adapt to a shape of a space into which the system is deployed, thereby minimizing potentially negative host interactions.

In accordance with various embodiments of the disclosure, a system includes a therapeutic agent—e.g., a molecule with medium to high hydrophobicity—that can be incorporated into the system in its liquid state by simple mixing. In this case, upon forming micelles and/or a gel, the therapeutic agent will preferentially gather at the hydrophobic sites of the system and be incorporated into the system. This will then provide a controlling mechanism for release of the therapeutic molecule, allowing for its sustained delivery over an extended period of time. Additionally or alternatively, one or more therapeutic agents may be encapsulated in or bonded to one or more supplemental therapeutic agent delivery systems to control the release of a therapeutic agent. These supplemental systems can be used to increase a duration of therapeutic agent delivery or otherwise control a rate of drug release, or to incorporate more than one therapeutic molecule (e.g., two molecules with different chemical properties) into the same system.

As compared to other reverse thermal gel systems, such as the RTG system disclosed in Park, D; Wu, W; Wang, Y. "A functionalizable reverse thermal gel based on a polyurethane/PEG block copolymer" *Biomaterials*, 32 (3), 777-86 (2011), various systems describe herein exhibit more favorable biodegradation properties. In particular, the degradation properties of various systems described herein allow for tailoring of the degradation rate to a specific therapeutic agent or specific disease process. In addition, exemplary systems are suitable for providing stable delivery of large molecules (e.g., biologics, peptides, and the like). As these molecules may degrade fairly rapidly upon exposure to non-physiologic pH or water, conventional systems such as PLGA-based nanoparticles are not ideal, due to their acidic degradation byproducts, which promote large molecule degradation.

In accordance with further exemplary embodiments of the disclosure, a system includes (optionally) one or more therapeutic agents, a reverse thermal gel (RTG), and one or more one or more supplemental therapeutic agent delivery systems (supplemental compounds) to further control release of a therapeutic agent. Exemplary supplemental compounds include one or more compounds selected from the group consisting of one or more nanoparticles, one or more micelle structures, and one or more liposomes. The combination of the RTG and the one or more compounds provides a controlling mechanism for sustained release of the one or more therapeutic agents. For example, the system may be configured to provide sustained release of the one or more therapeutic agents for greater than 3 months, greater than 4 months, 3-12 months, 3-6 months, 4-6 months, or greater than 12 months.

Another advantage of a system including an RTG and one or more supplemental systems, also referred to herein as supplemental compounds, to control the release of a therapeutic agent is an ability to tailor the composition of the system for desired therapeutic agent release characteristics. The RTG compound can be designed, for example, to facilitate sharp, reproducible transitions at a temperature slightly below body temperature and to control a degradation rate of the RTG. The one or more supplemental compounds can be designed to further control the rate of release of the therapeutic agent(s). By controlling these parameters independently, desired properties of the system, such as minimally-invasive deployment, sustained drug release on the scale of several months to years, extremely high biocompatibility, and biodegradation on a time scale similar to release of the entire drug payload, may be obtained.

In accordance with other embodiments of the disclosure, the system includes an RTG as described herein and optionally one or more therapeutic agents. These systems do not necessarily, but may include one or more supplemental compounds to further control release of a therapeutic agent—for example one or more compounds selected from the group consisting of one or more nanoparticles, one or more micelle structures, and one or more liposome systems.

In accordance with yet further embodiments, micelles compounds, which may optionally be loaded with one or more therapeutic agents are disclosed. The micelle compounds may be used in combination with an RTG as described herein.

Exemplary reverse thermal gels in accordance with the present disclosure include a copolymer, which is water soluble and biodegradable and which includes hydrophobic and hydrophilic portions prior to gelling. By way of particular examples, the RTG includes a graft copolymer, having a backbone based on poly[hexamethylene-alt-(serinol; urea)] (PHSU).

repeating unit of PHSU a Boc-protected amine functionality. When the Boc group is removed, a primary amine is left, which can be used for conjugating various molecules. Because of the relative frequency of these Boc groups (around 18 repeating units per exemplary PHSU molecule), a significant amount of conjugation can take place.

For example, the primary amines may be used as the sites for conjugating PNIPAAm to the PHSU backbone. Exemplary PNIPAAm structures are shown below.

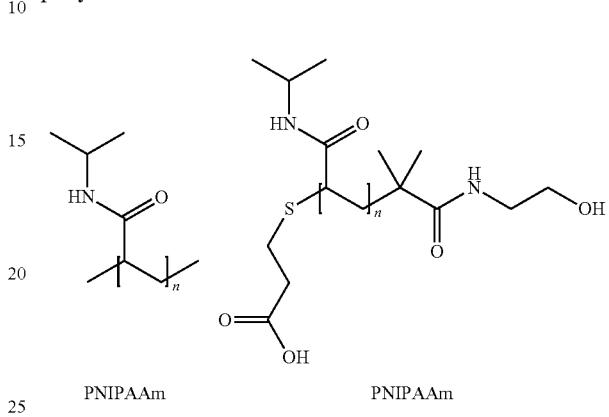

PNIPAAm          PNIPAAm

An amount of PNIPAAm conjugated to the backbone can be controlled by, for example, 1) controlling the de-protection procedure in such a way that less than 100% of the Boc functional groups are removed opening up fewer primary amines for attachment or 2) deprotecting all of the Boc functional groups, but less than 100% of available primary amines are actually conjugated by PNIPAAm (where x/(x+y) defines the conjugation ratio). In both cases, it is the conjugation ratio of PNIPAAm to PHSU that is being controlled. Exemplary conjugation ratios range from about 10% to about 100%, including 10% to 100%. The only structural difference in the final product between these two approaches is whether or not un-protected primary amines are present. If present, these amines will allow for further conjugation of, for example, biomacromolecules or other

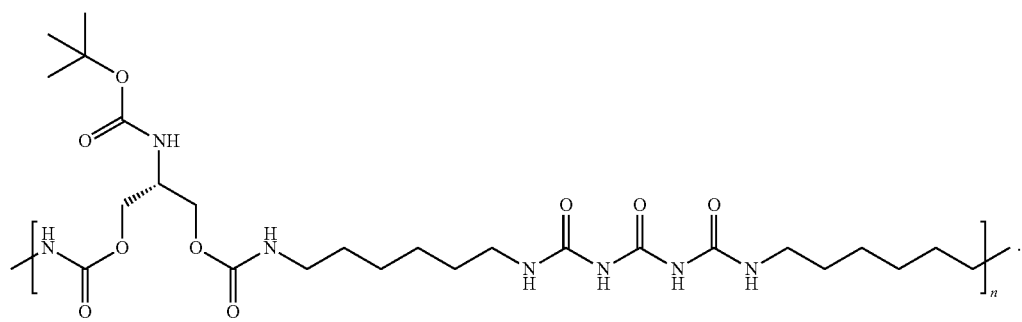

PHSU, showing protecting Boc group and protected amine functionality

Figure 11:
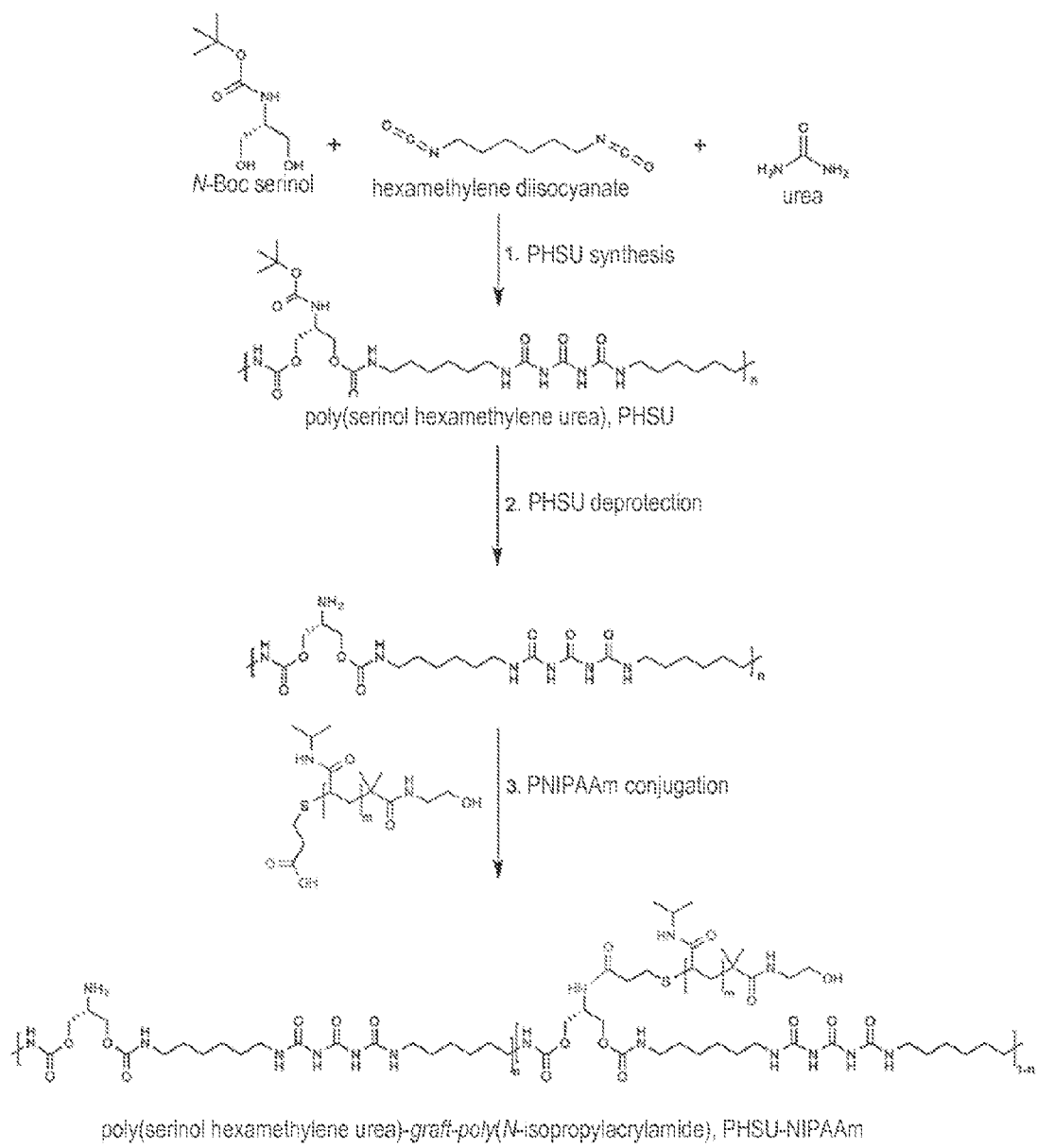
FIG. 11 illustrates a method of forming a graft copolymer: poly[hexamethylene-alt-(serinol; urea)]graft-poly(N-isopropylacrylamide) (PHSU-PNIPAAm) in accordance with additional exemplary embodiments of the disclosure.

Used as a backbone in a copolymer, PHSU has several desirable characteristics that may be used advantageously in the exemplary systems. For example, PHSU has distinct biomimetic characteristics, owing to extensive amide ester bonding. As a result, FT-IR spectra of PHSU and natural polymers such as collagen show very similar peaks. In addition, the use of N-Boc serinol as a monomer gives every therapeutic agents, if desirable. Exemplary methods of forming PHSU-PNIPAAm are illustrated in FIG. 1 and FIG. 11, and are described in more detail below in connection with various examples. Exemplary resulting polymers are graft copolymers: poly[hexamethylene-alt-(serinol; urea)]-graft-poly(N-isopropylacrylamide) (PHSU-PNIPAAm), exemplary structures of which are below.

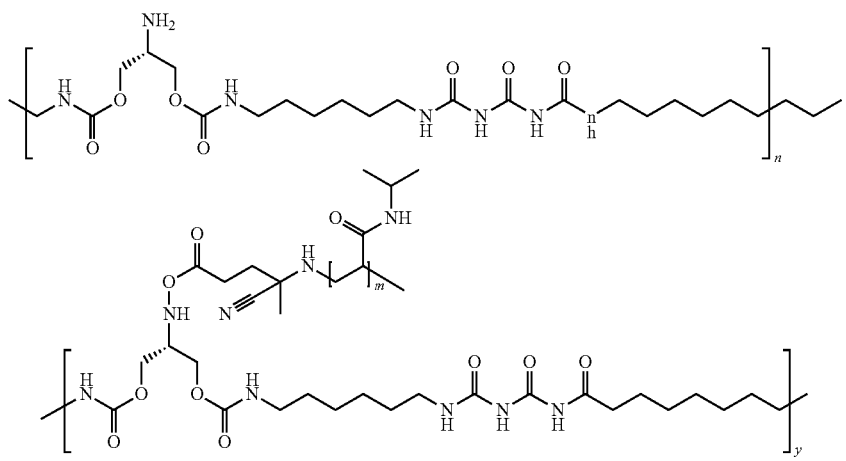

Exemplary structure of PHSU-PNIPAAM copolymer

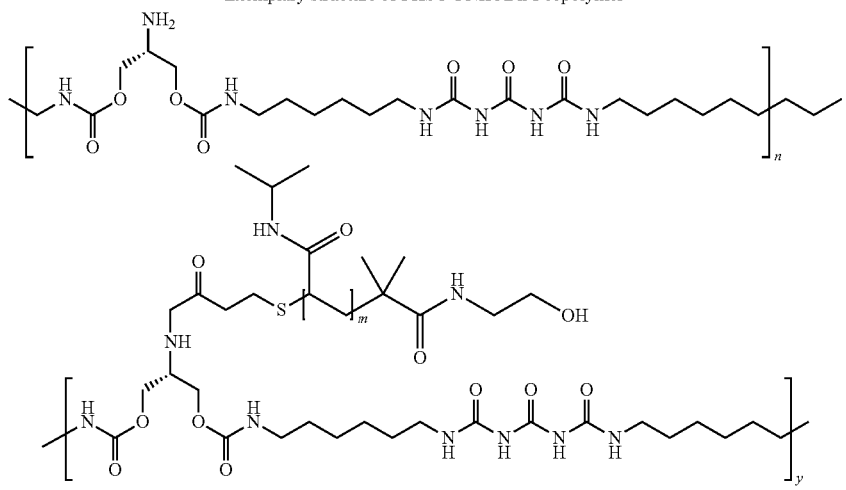

Exemplary structure of PHSU-PNIPAAM copolymer

Another suitable backbone polymer for the various reverse thermal gels described herein is esterified PHSU (termed esterified PHSU or ePHSU). The esterified PHSU backbone may provide a more-rapidly biodegrading chemistry. Esterified PHSU may be obtained by synthesizing PHSU in a manner that introduces ester bonds throughout the polymer structure, the hydrolytic cleavage of which accelerates its rate of biodegradation. The structure of ePHSU is shown below. In this case, the resulting RTG is not a grafted structure, but a linear block copolymer, with PNIPAAm-COOH conjugated through the primary amine functionalities present at each end of ePHSU. The synthetic route is slightly different for this polymer and has also been outlined below.

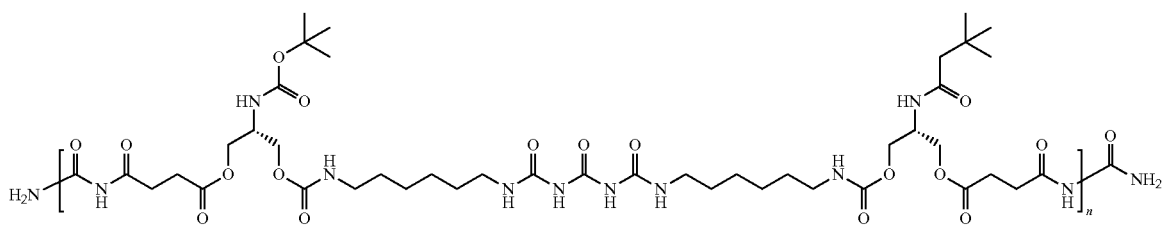

Exemplary structure of PHSU-PNIPAAM linear block copolymer

As set forth in more detail below, in accordance with additional aspects of various embodiments, a delivery system may include one or more supplemental therapeutic agent delivery systems, such as one or more nanoparticles (polymeric or non-polymeric), one or more micelle compounds, one or more liposome systems, or a combination thereof. In cases when the system includes liposome systems, micelle compounds or nanoparticles, therapeutic agent(s) may be loaded into the micelle compounds and/or liposome systems and/or attached to nanoparticles and a combination of the therapeutic agent(s) and the micelle compound(s) and/or nanoparticles and/or liposome systems may be added to the reverse thermal gel composition. Additionally or alternatively, therapeutic agents may be bonded to or grafted onto portions of the reverse thermal gels as described herein.

Polymeric micelle compounds suitable for use in accordance with exemplary embodiments include amphiphilic polymers. In an aqueous environment, hydrophobic interactions drive the hydrophobic segments of the polymer to aggregate together to be surrounded by the hydrophilic segments. For this organization to occur, there is generally sufficient chain mobility for the hydrophilic and hydrophobic segments to largely distance themselves from each other.

Exemplary micelle-forming polymers include diblock and triblock copolymers, with a diblock copolymer including one hydrophobic block and one hydrophilic block and a triblock copolymer including a hydrophobic middle segment surrounded by two hydrophilic segments. Other micelle-forming polymers suitable for use in accordance with various embodiments of the disclosure include graft copolymers, in which a hydrophilic polymer segment is grafted to a hydrophobic polymer segment. The micelles may self align—for example, when exposed to an aqueous solution. The micelle structures themselves (i.e., without addition of a reverse thermal gel) may provide a system for releasing a therapeutic agent over an extended period of time, such as, for example, a period of more than three months.

Exemplary micelle polymers include a hydrophobic block having a molecular weight of about 47000 Da to about 200000 Da or about 47000 Da. The hydrophilic block(s) may have a molecular weight of about 500 Da to about 2000 Da or about 550 Da.

A choice of polymers employed for the hydrophobic and hydrophilic segments may determine, at least in part, the properties of the micelles formed from the copolymer. In the case of micelles used for biomedical applications, the hydrophilic block polymer is typically on a surface of the micelle and may interact with the surrounding physiological environment. Exemplary hydrophilic polymers include, for example, one or more polymers selected from the group consisting of polyethylene glycol, polyether, polyacrylamide or poly(vinyl alcohol) compounds and exemplary hydrophobic polymers include, for example, one or more polymers selected from the group consisting of poly (hexamethylene-alt-serinol) (PHS) (e.g., synthesized by the reaction of hexamethylene diisocyanate and N-Boc serinol.), poly(ester urethane), polyamide, polycarbonate, polyurea, polyacrylate, polyester, polystyrene or polyvinyl compounds. A chain length of the hydrophilic polymer may range from about 500 to about 800 or about 400 to about 1000 and a chain length of the hydrophobic polymer may range from about 30000 to about 100000 or about 10000 to about 200000. A chain length of the hydrophobic polymer may be greater (e.g., by about 1.2 to about 6.0) relative to the chain length of the hydrophilic polymer.

In accordance with particular illustrative embodiments of the disclosure, a micelle-forming polymer includes highly biocompatible polyethylene oxide (a.k.a. polyethylene glycol, PEG) as the hydrophilic segments in a block copolymer. PEG lends a polar shell to the micelle, facilitating solubility in water and preventing the adsorption of proteins, thereby significantly reducing its clearance rate. The hydrophobic segment may include, for example, a polyurethane synthesized from N-Boc serinol (NBS) and hexamethylene diisocyanate (HDI), named poly(hexamethylene-alt-serinol) (PHS), the structure of which is shown below.

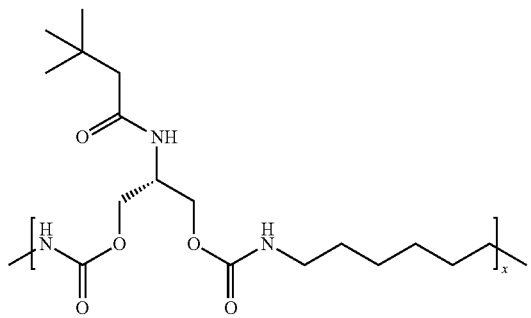

PHS structure

In the formulation of polyurethanes, diisocyanates are often used because of their ability to produce high molecular weight polymers without the use of catalysts. In one example, hexamethylenes introduced by HDI lend hydrophobicity to the resulting polymer. While diisocyanates are traditionally coupled with diols, the choice of the diol NBS in this case may be desirable due to the highly hydrophobic Boc functionality, which contains three methyl groups attached to the same carbon atom. In addition, the ability to remove this Boc functional group, if desired, opens up a primary amine group, which can be used to conjugate therapeutic agents (e.g., biomolecules) directly to the polymer backbone. The relatively high hydrophobicity of the resulting polyurethane forms a stable micelle core that can efficiently encapsulate and control the release of hydrophobic drug molecules, such as triamcinolone acetonide (log P=1.16).

Below is an exemplary triblock copolymer used for fabricating drug-eluting micelles (also referred to herein as micelle structures).

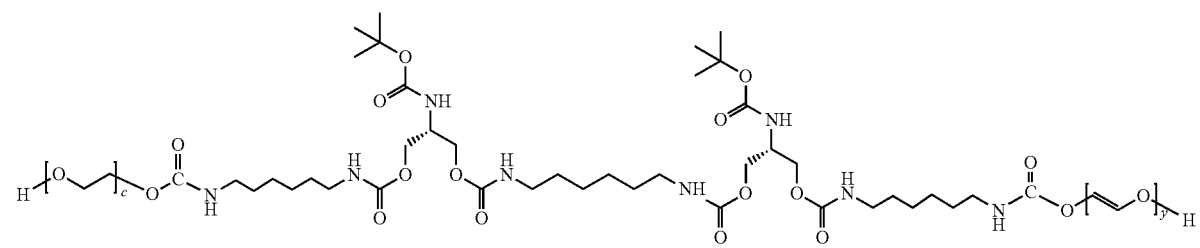

In accordance with various embodiments of the disclosure, the systems include on or more therapeutic agents.

Exemplary therapeutic agents include: anti-fibrotic agent, anti-inflammatory agent, immunosuppressant agent, anti-neoplastic agent, migration inhibitors, anti-proliferative agent, rapamycin, triamcinolone acetonide, everolimus, tacrolimus, paclitaxel, actinomycin, azathioprine, dexamethasone, cyclosporine, bevacizumab, an anti-VEGF agent, an anti-IL-1 agent, canakinumab, an anti-IL-2 agent, viral vectors, beta blockers, alpha agonists, muscarinic agents, steroids, antibiotics, non-steroidal anti-inflammatory agents, prostaglandin analogues, ROCK inhibitors, nitric oxide, endothelin, matrixmetalloproteinase inhibitors, CNPA, corticosteroids, an antibody-based immunosuppressants, medications that decrease eye pressure, medications that decrease edema in and around the eye, medications that treat neovascular diseases of the eye, and any combination thereof.

The systems described herein may be used to treat a variety of conditions, including glaucoma, age related macular disease, uveitis, neuropathies, non-arteritic ischemic optic neuropathy, arteritic ischemic optic neuropathy, retinal vein occlusion, arterial occlusion, diabetic retinopathy, congential retinal/choroidal dystophies, inherited retinal/choroidal dystrophies, acquired retinal/choroidal dystrophies, basic and acidic burn injuries, trauma, hyphema, conjunctivitis, corneal dystrophies, Fuchs dystrophy, cataract, ocular and periocular malignancies, strabismus, epiphora, dry eye syndrome, sjogrens syndrom, ocular cicatricial pemphigoid, meibomian gland dysfunction, thyroid eye disease, and cystoid macular edema. The conditions may include disorders of eyelid, lacrimal system and orbit, disorders of conjunctiva, disorders of sclera, cornea, iris and ciliary body, disorders of lens, disorders of choroid and retina chorioretinal inflammation, other disorders of choroid, chorioretinal disorders in diseases classified elsewhere, retinal detachments and breaks, retinal vascular occlusions, other retinal disorders, retinal disorders in diseases classified elsewhere, disorders of vitreous body and globe, disorders of optic nerve and visual pathways, disorders of ocular muscles, binocular movement, accommodation and refraction, visual disturbances and blindness, and other disorders of the eye and adnexa.

Methods of treatment in accordance with various embodiments of the disclosure include a step of injecting a therapeutic agent delivery system as described herein into a patient in need of treatment. The step of injecting may include injecting the therapeutic agent delivery system into an eye. In this case, the system may be delivered via an intravitreal injection. In accordance with various aspects of these embodiments, the therapeutic agent delivery system is delivered via injection into one or more of the periocular spaces. In accordance with further aspects, the therapeutic agent delivery system is delivered via injection at or near the optic nerve. In accordance with yet further aspects, the step of injecting includes injecting the therapeutic agent delivery system into an implanted device, which may be located within an eye.

EXAMPLES

The following non-limiting examples illustrate exemplary systems and components thereof in accordance with various embodiments of the disclosure. These examples are merely illustrative, and it is not intended that the disclosure be limited to these examples.

Synthesis of PNIPAAm-COOH

PNIPAAm is synthesized by a free radical polymerization using the thermal initiator 4,4'-azobis(4-cyanovaleric acid) (ACA), which lends a carboxylic acid functionality to only one end of the resulting polymer. N-isopropylacrylamide (NIPAAm, Sigma-Aldrich, St. Louis, Mo.) is dissolved in anhydrous N,N-dimethylformamide (DMF, Sigma-Aldrich) to form a 0.5 g/mL solution in a round-bottom flask (RBF). ACA (Sigma-Aldrich) is added to this solution at 1.2 wt % (ACA/NIPAAm). Dry nitrogen gas is bubbled through this reaction mixture for 30 minutes at room temperature to de-gas the solution. The flask is sealed under a nitrogen atmosphere and the reaction is heated to 68° C. The reaction is carried out for 3 hours under gentle stirring. Purification is carried out by three washes in 60° C. water (milliQ or equivalent) followed by dialysis against 1 L water for 24 hours (dialysis membrane MWCO: 3.5 kDa, Spectrum Labs, Rancho Dominguez, Calif.). The product is lyophilized at −45° C. and 0.045 mbar for 48 hours to yield PNIPAAm-COOH.

Synthesis of HO-PNIPAAm-COOH

In this case, PNIPAAm is synthesized via a reversible addition-fragmentation chain transfer (RAFT) polymerization. This permits precise control over two properties that are thought to be modulators of PNIPAAm LCST: molecular weight and end group hydrophobicity. In order to achieve a sufficiently high LCST, both end groups were made relatively hydrophilic by employing: a) the water-soluble azo initiator AMHP, lending the polymer one hydroxyl end group; and b) MPA as a CTA, capping the other end of the polymer with a carboxylic acid.

Figure 12:
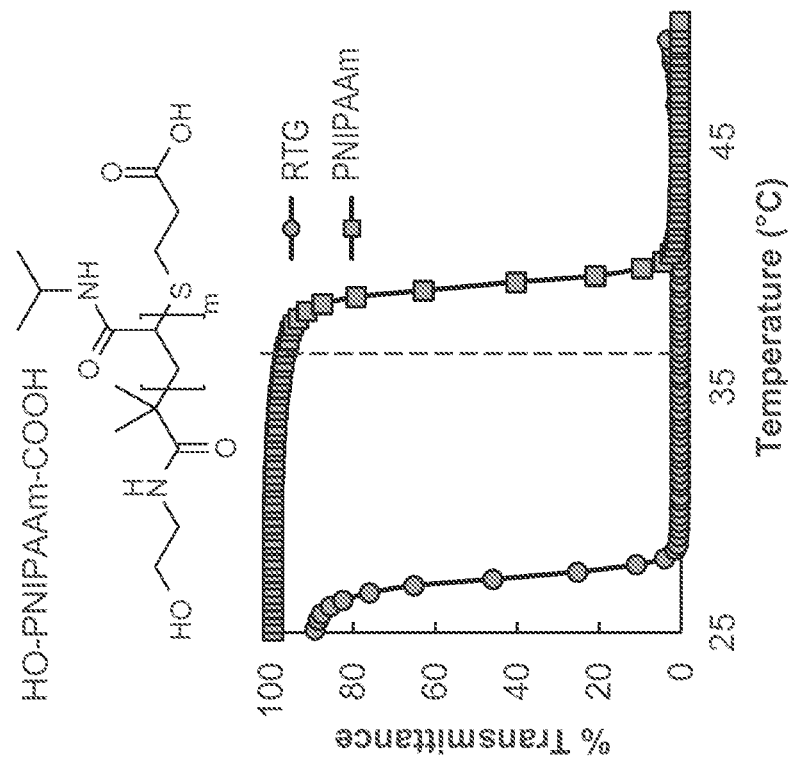
FIG. 12 illustrates a dependence of LCST on molecular weight for PNIPAAm chemistry (PNIPAAm-COOH) with only one controlled carboxyl end group and for a heterobifunctional PNIPAAm (HO-PNIPAAm-COOH).
Figure 14:
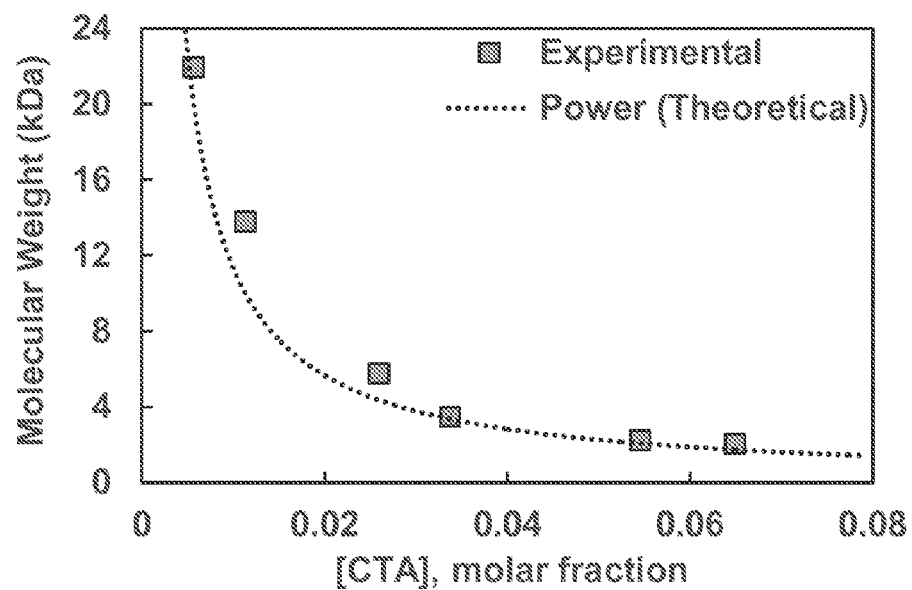
FIG. 14 illustrates experimental and theoretical molecular weight of synthesized HO-PNIPAAm-COOH vs. the molar fraction of CTA.

FIG. 12 illustrates a dependence of LCST on molecular weight for PNIPAAm chemistry (PNIPAAm-COOH) with only one controlled carboxyl end group and for a heterobifunctional PNIPAAm (HO-PNIPAAm-COOH). As illustrated, HO-PNIPAAm-COOH provides a significant increase in the LCST of PNIPAAm, with low molecular weight variants displaying an LCST as high as 49.4° C. Molecular weights up to 22.0 kDa still afforded an LCST above body temperature, permitting a wide range of usable polymers that are soluble at body temperature. In addition, the RAFT polymerization developed to achieve this kinetic yielded polymers within 20% of the target molecular weight (illustrated in FIG. 14), indicating a robust polymerization process. Thus, HO-PNIPAAm-COOH can be used to form a cleavable portion of a graft copolymer that will be soluble at body temperatures.

Synthesis of PHSU

With reference to FIG. 1 and FIG. 11, PHSU is synthesized by an isocyanate-mediated urethane polymerization. Urea and N-Boc-serinol (Sigma-Aldrich) in a 1:1 molar ratio are weighed out and lyophilized in an RBF for 12 hours at −45° C. and 0.045 mbar. The flask is sealed with a nitrogen atmosphere, anhydrous DMF is added to form a 0.16 g/mL solution and the reaction is heated to 90° C. under gentle stirring. Upon achieving a stable temperature, hexamethylene diisocyanate (HDI, Sigma-Aldrich) is added at a 3:1 molar ratio (HDI:urea) and the reaction is carried out for 7 days. Purification is carried out by three precipitations in diethyl ether (Sigma-Aldrich) and three washes in water (milliQ or equivalent) under gentle sonication. The product is lyophilized at −45° C. and 0.045 mbar for 24 hours to yield PHSU.

Figure 15:
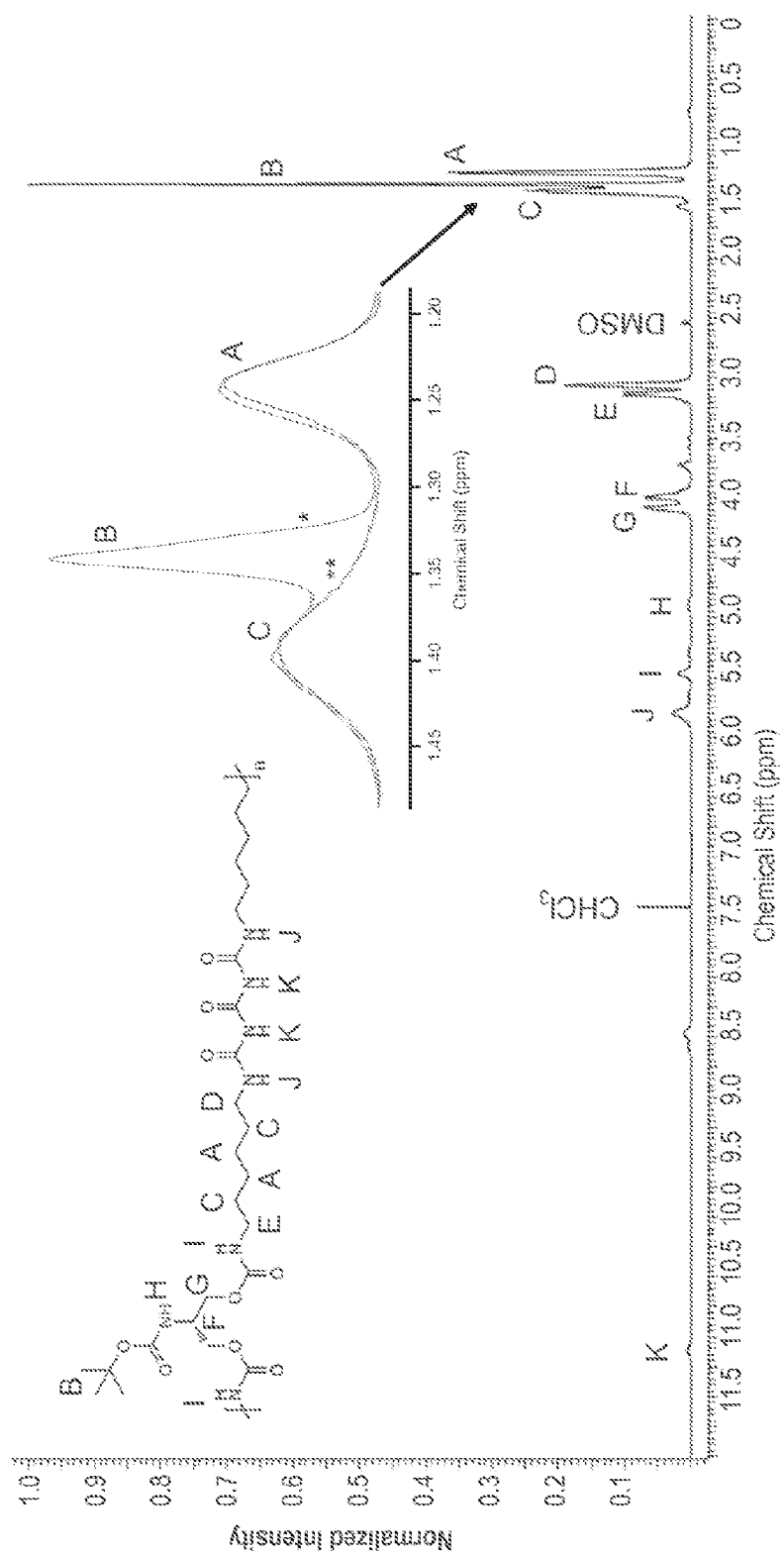
FIG. 15 illustrates structural characterization of the PHSU polymer via $^1$H NMR.

Structural characterization of the PHSU polymer via $^1$H NMR is illustrated in FIG. 15. The $^1$H NMR characterization confirmed the copolymer structure incorporating urea segments, urethane segments and protected primary amine functionalities that could be selectively removed by a mild acid treatment.

De-Protection of PHSU

With continued reference to FIG. 1 and FIG. 11, de-protection of PHSU is achieved by treatment with a strong acid for a short period of time, cleaving the ester linkages attaching the Boc groups to the primary amines PHSU is dissolved in equal volumes of trifluoroacetic acid (TFA, Sigma-Aldrich) and dichloromethane (DCM, Sigma-Aldrich) and stirred at room temperature for one hour. The reaction is terminated by removing TFA and DCM by rotary evaporation at 70° C. and 10 mbar. The resulting polymer is re-dissolved in DMF and purified by three precipitations in diethyl ether. The product is dried to a powder by extended rotary evaporation to yield dPHSU.

Conjugation of PNIPAAm-COOH to dPHSU

As illustrated in FIG. 1, PNIPAAm-COOH can be conjugated to dPHSU by a carbodiimide-mediated reaction between the terminal carboxylic acid of PNIPAAm-COOH and the de-protected primary amines of dPHSU. PNIPAAm-COOH is dissolved in anhydrous DMF in a RBF, to which 3 molar excesses of N-hydroxysuccinimide and N-(3-dimethylaminopropyl)-N'-ethylcarbodiimide hydrochloride (EDC-HCl, Sigma-Aldrich) are added. The reaction is carried out at room temperature under a nitrogen atmosphere and gentle stirring for 24 hours to form the PNIPAAm-NHS ester. dPHSU is added at the molar quantity necessary to conjugate PNIPAAm to 25% of the de-protected primary amines on dPHSU. This reaction is then continued for another 24 hours. Purification is carried out by three precipitations in diethyl ether followed by dialysis against 1 L water for 24 hours (MWCO: 3.5 kDa). The product is lyophilized at −45° C. and 0.045 mbar for 48 hours to yield PHSU-PNIPAAm.

Conjugation of HO-PNIPAAm-COOH to dPHSU

Figure 13:
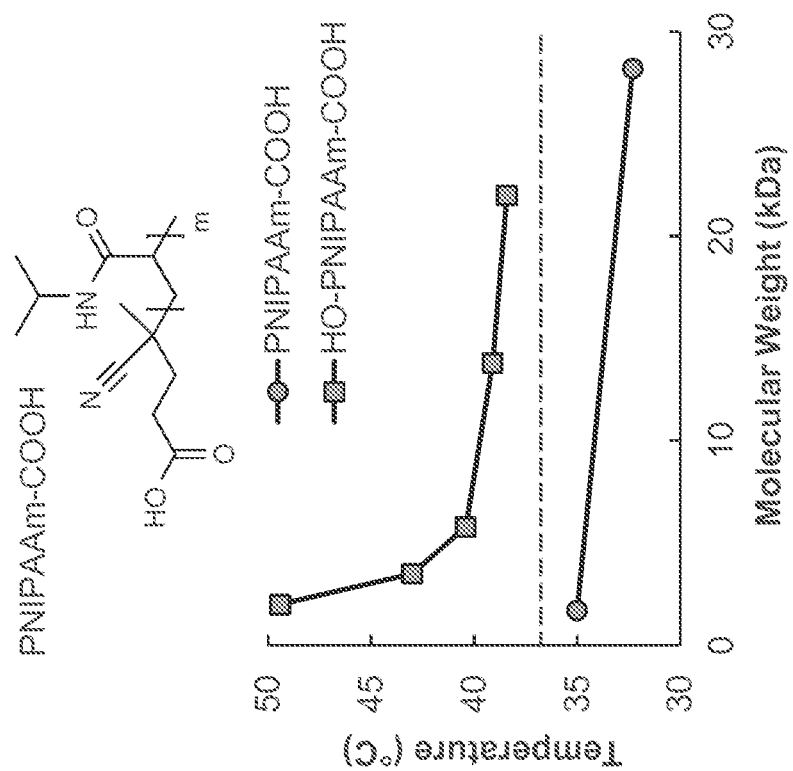
FIG. 13 illustrates a shift in LCST of HO-PNIPAAm-COOH after conjugation to a PHSU backbone.

As illustrated in FIG. 13, the LCST of HO-PNIPAAm-COOH chemistry was shifted below body temperature upon conjugation to the PHSU backbone polymer. In the illustrated example, LCST of 13.8 kDa PNIPAAm was driven from 39.1° C. before conjugation to 26.7° C. after conjugation, indicating the copolymer can undergo thermal gelation upon introduction to body temperature. This result can be attributed to two consequences of the conjugation procedure. The first is that the carbodiimide chemistry used to conjugate PNIPAAm to PHSU consumes the carboxylic acid terminal of PNIPAAm, resulting in one less hydrophilic end group on the polymer. The second is that the PHSU backbone is relatively hydrophobic. As such, after conjugation it acts as a high molecular weight hydrophobic end group, which drives the LCST to lower temperatures. The combination of these effects results in the dramatic LCST decrease observed after conjugation and permits physiological gelation of the copolymer.

Figure 16:
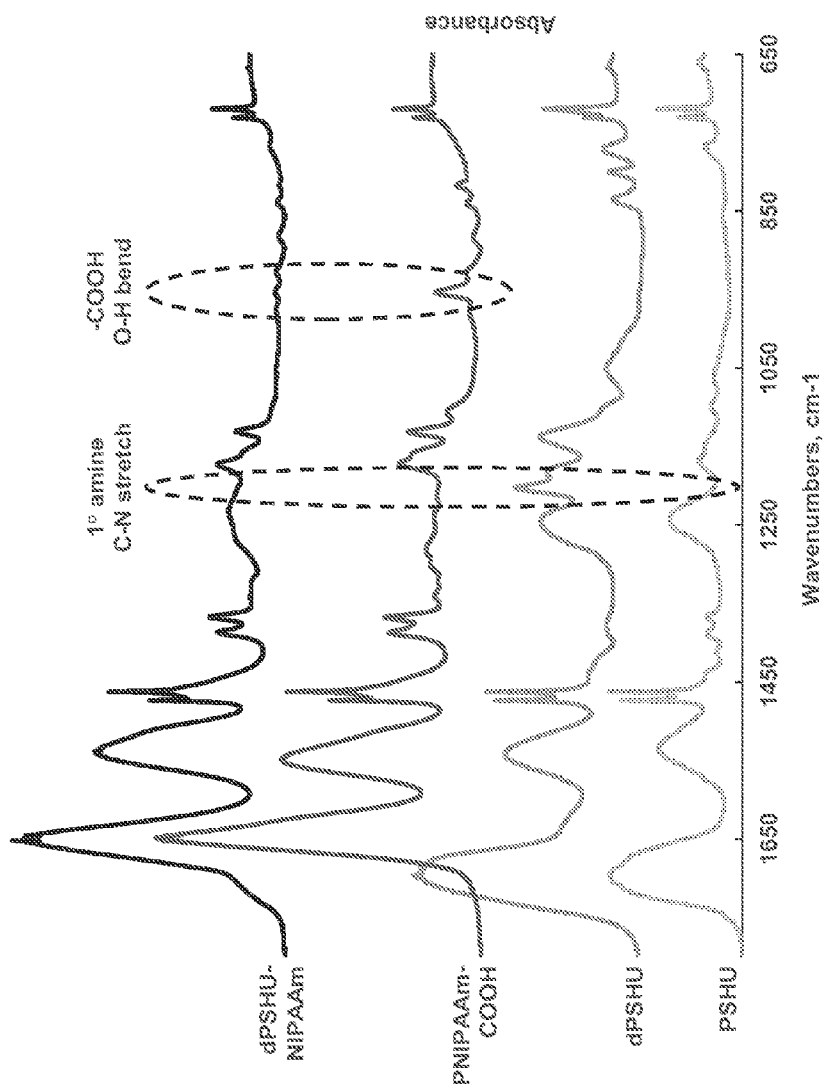
FIG. 16 illustrates FT-IR analyses of PHSU polymers and a copolymer, showing conjugation in PHSU-NIPAAm through the peaks at 1650-1700 cm-1 (A, amide C=O stretch), 950 cm-1 (B, carboxyl O—H bend) and 798 cm-1 (C, primary amine N—H wag).

PNIPAAm conjugation to PHSU was confirmed by FT-IR characterization, illustrated in FIG. 16, and the average conjugation ratio was inferred from elemental analysis data to be 3.2 PNIPAAm molecules per PHSU molecule as illustrated below in Table 1.

TABLE 1

|  | % C | % H | % N | % O |
| --- | --- | --- | --- | --- |
| dPHSU | 50.35 | 7.96 | 15.77 | 23.59 |
| PHSU | 42.77 | 6.60 | 15.07 | 28.58 |
| PNIPAAm | 62.90 | 9.64 | 12.82 | 14.64 |
| PHSU-NIPAAm | 59.56 | 10.15 | 12.04 | 18.01 |

Synthesis of Esterified PHSU

To synthesize esterified PHSU, small molecular weight oligomers of PHSU are first synthesized and then coupled together using ester-containing linkages and urea. Urea and N-Boc-serinol (Sigma-Aldrich) in a 1:1 molar ratio are weighed out and lyophilized in an RBF for 12 hours at −45° C. and 0.045 mbar. The flask is sealed with a nitrogen atmosphere, anhydrous DMF is added to form a 0.16 g/mL solution and the reaction is heated to 90° C. under gentle stirring. Upon achieving a stable temperature, hexamethylene diisocyanate (HDI, Sigma-Aldrich) is added at a 3:1 molar ratio (HDI:urea) and the reaction is carried out for 6 hours. N-Boc Serinol is added in a 2 molar excess and the reaction is continued for another 12 hours (to cap each end of the oligomer with terminal hydroxyl groups). Purification is carried out by three precipitations in diethyl ether (Sigma-Aldrich) and two washes in water (milliQ or equivalent) under gentle sonication. The product is lyophilized at −45° C. and 0.045 mbar for 24 hours to yield PHSU-OH. To convert the terminal hydroxyl groups to carboxylic acids and introduce ester linkages, PHSU-OH is dissolved in anhydrous DMF and heated to 50° C. under gentle stirring and a nitrogen atmosphere. Three molar excesses each of succinic anhydride (SA, Sigma-Aldrich) and 4-dimethylaminopyridine (DMAP, Sigma-Aldrich) are added and this reaction is carried out for 12 hours at room temperature. Three molar excesses of NHS and EDC-HCl are then added and reacted for another 24 hours, after which urea is added at a 1:1 molar ratio with the starting PHSU-OH and reacted for a further 4 days. More urea is added at a 3 molar excess and reacted for 24 hours to cap all ends with primary amine groups. Purification is carried out by three precipitations in diethyl ether (Sigma-Aldrich) and three washes in water (milliQ or equivalent) under gentle sonication. The product is lyophilized at −45° C. and 0.045 mbar for 24 hours to yield ePHSU.

Conjugation of PNIPAAm-COOH to ePHSU

With this esterified PHSU capped with urea at each end, the terminal primary amines can be used to conjugate PNIPAAm-COOH through a carbodiimide-mediated reaction. PNIPAAm-COOH is dissolved in anhydrous DMF in a RBF, to which 3 molar excesses of N-hydroxysuccinimide and N-(3-dimethylaminopropyl)-N'-ethylcarbodiimide hydrochloride (EDC-HCl, Sigma-Aldrich) are added. The reaction is carried out at room temperature under a nitrogen atmosphere and gentle stirring for 24 hours to form the PNIPAAm-NHS ester. ePHSU is added at a 1:3 molar ratio (ePHSU:PNIPAAm-COOH) and the reaction is continued for another 24 hours. Purification is carried out by three precipitations in diethyl ether followed by dialysis against 1 L water for 24 hours (MWCO: 12-14 kDa). The product is lyophilized at −45° C. and 0.045 mbar for 48 hours to yield ePHSU-PNIPAAm.

Forming the RTG

A reverse thermal gel, e.g., PHSU-PNIPAAm or ePHSU-PNIPAAm is formed by dissolving the dry polymer in a volume of water and then activated by increasing the temperature of the solution. (If desired, a therapeutic agent, such as TA can be added by suspending the agent in the RTG solution before activation.) While the concentration of the RTG solution can be adjusted to achieve various desired properties (room temperature viscosity, gelling time, density of RTG matrix, etc.), a 5 to 10 wt % (polymer/solution) solution produces a good balance of room temperature viscosity and gelling time. For example, to produce 1 mL of a 5 wt % solution, 50 mg of the polymer is weighed out in a small vial and 950 μL of dH2O is added. The polymer is dissolved overnight at 4° C. To activate the RTG, the solution is heated to 37° C. and to reform the solution it is cooled back to room temperature. In the illustrated cases, activation and re-dissolution take about 20 seconds each.

Figure 5:
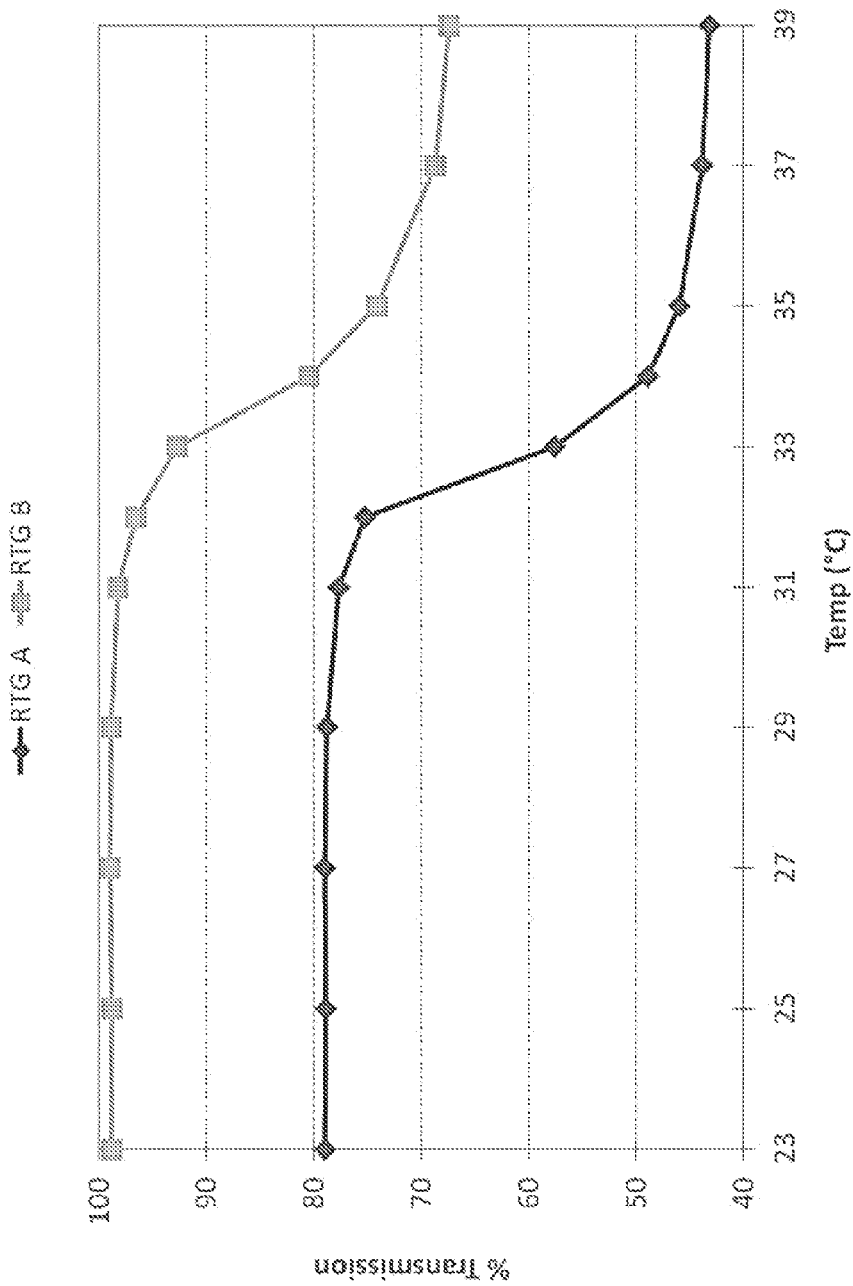
FIG. 5 illustrates lower critical solution temperatures (LCST) of reverse thermal gels in accordance with exemplary embodiments of the disclosure.

FIG. 5 illustrates lower critical solution temperature measurements of PNIPAAm-COOH-PHSU based RTGs as determined by UV-visible spectroscopic measurements. In the illustrated example, RTG A has 100% conjugation ratio and RTG B has 25% conjugation ratio.

Figure 6:
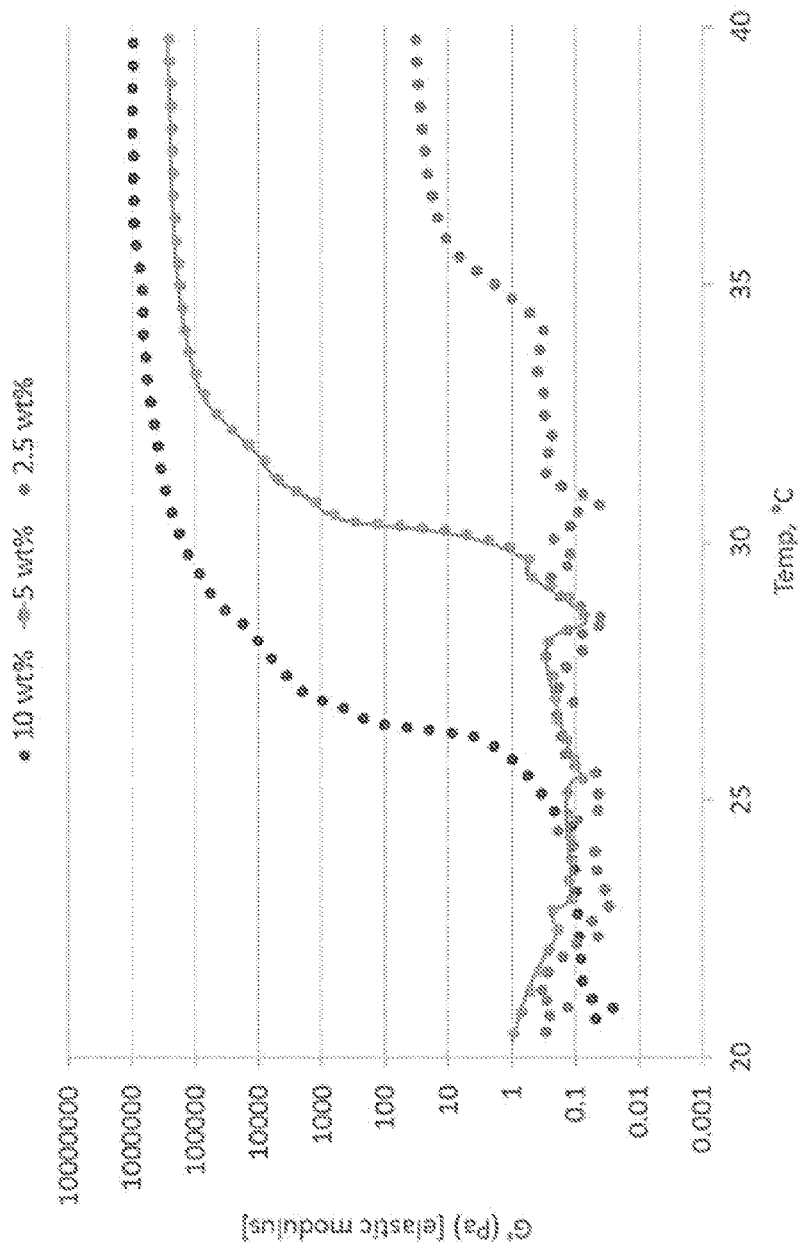
FIG. 6 illustrates temperature dependent behavior of G' of various concentrations of a reverse thermal gel in a phosphate-buffered solution in accordance with exemplary embodiments of the disclosure.
Figure 7:
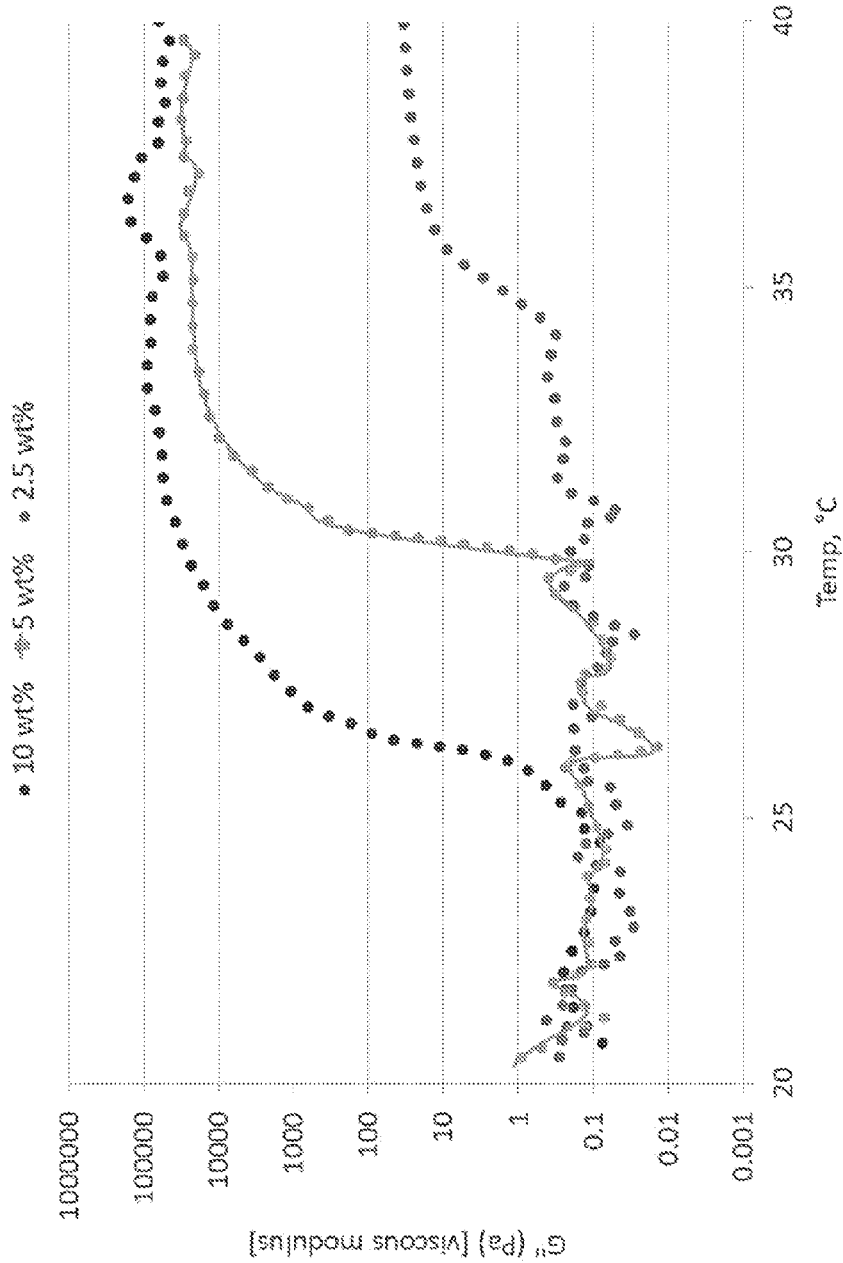
FIG. 7 illustrates temperature dependent behavior of G" of various concentrations of a reverse thermal gel in a phosphate-buffered solution in accordance with exemplary embodiments of the disclosure.

FIG. 6 illustrates temperature-dependent behavior of G', the elastic/solid component of the modulus, of PNIPAAm-COOH-PHSU based RTGs as determined by rheological analysis. FIG. 7 illustrates the temperature dependent behavior of G", the viscous/liquid component of modulus as determined by rheological analysis.

Figure 9:
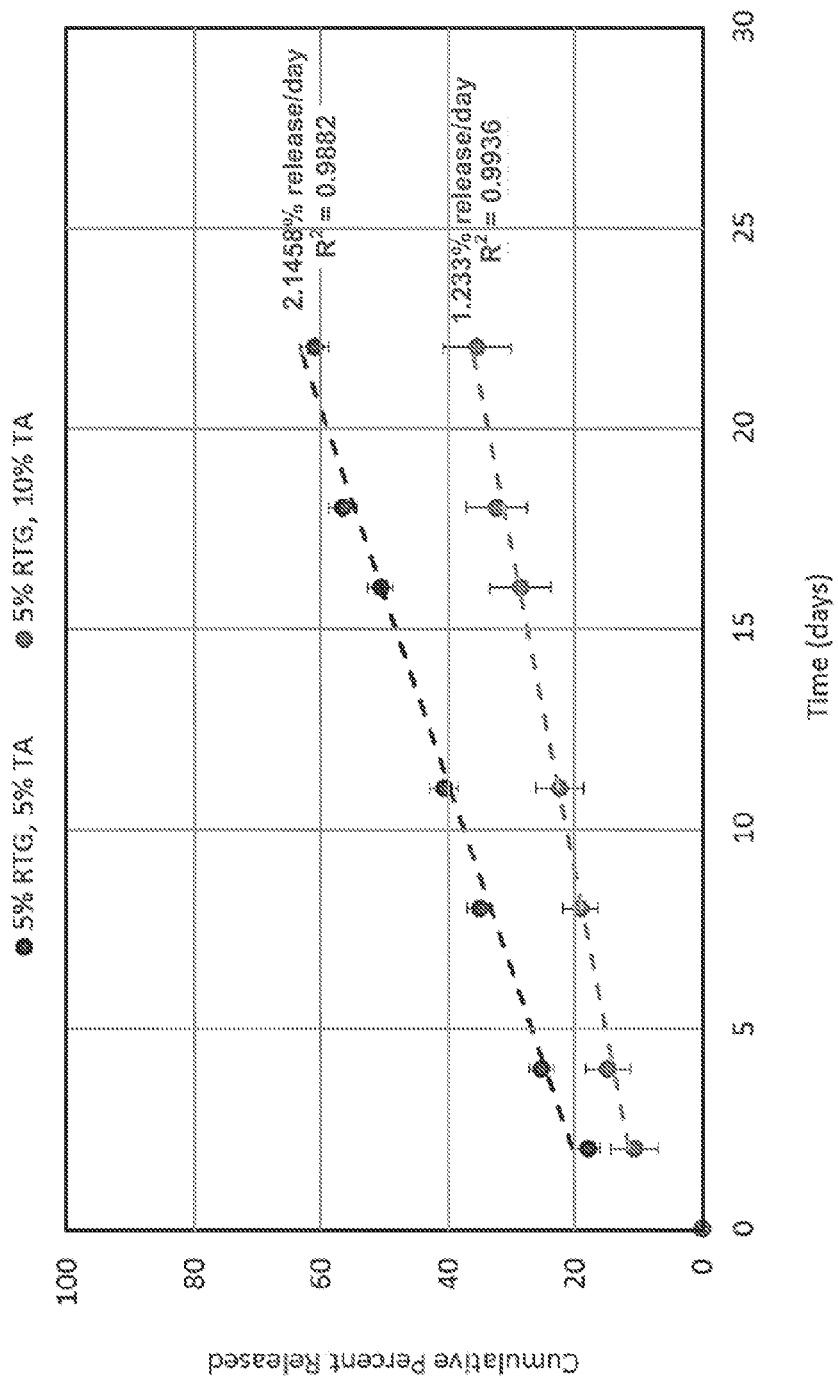
FIG. 9 illustrates release of triamcinolone acetonide from a reverse thermal gel in accordance with exemplary embodiments of the disclosure.

FIG. 9 illustrates release of triamcinolone acetonide (5 and 10 wt % loading) from an exemplary PNIPAAm-COOH-PHSU based RTG with a 25% conjugation ratio.

Figure 10:
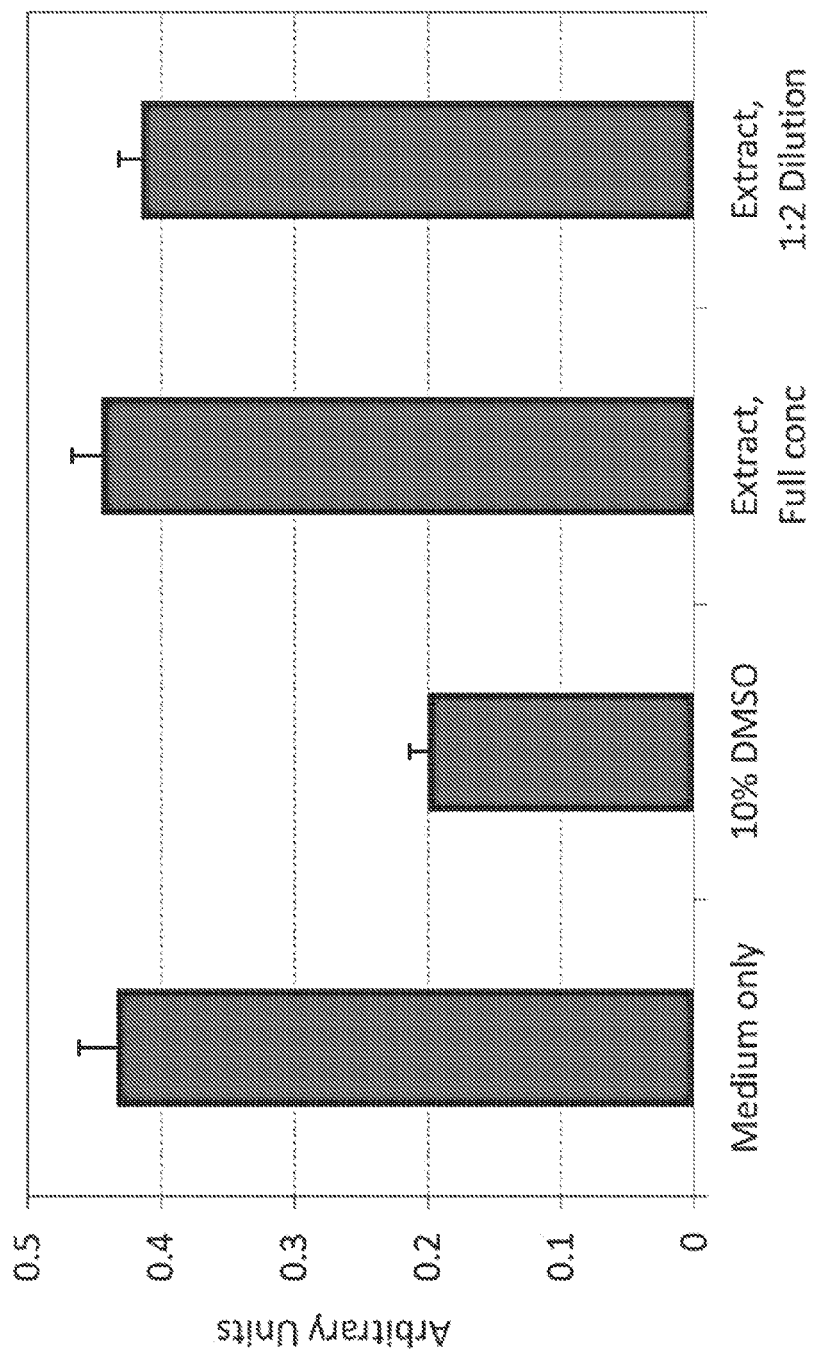
FIG. 10 illustrates cytotoxicity results of a PHSU-PNIPAAm reverse thermal gel in accordance with exemplary embodiments of the disclosure.

FIG. 10 illustrates a cytotoxicity of a PNIPAAm-COOH-PHSU based RTG.

Synthesis of Drug-Eluting Micelles

Figure 2:
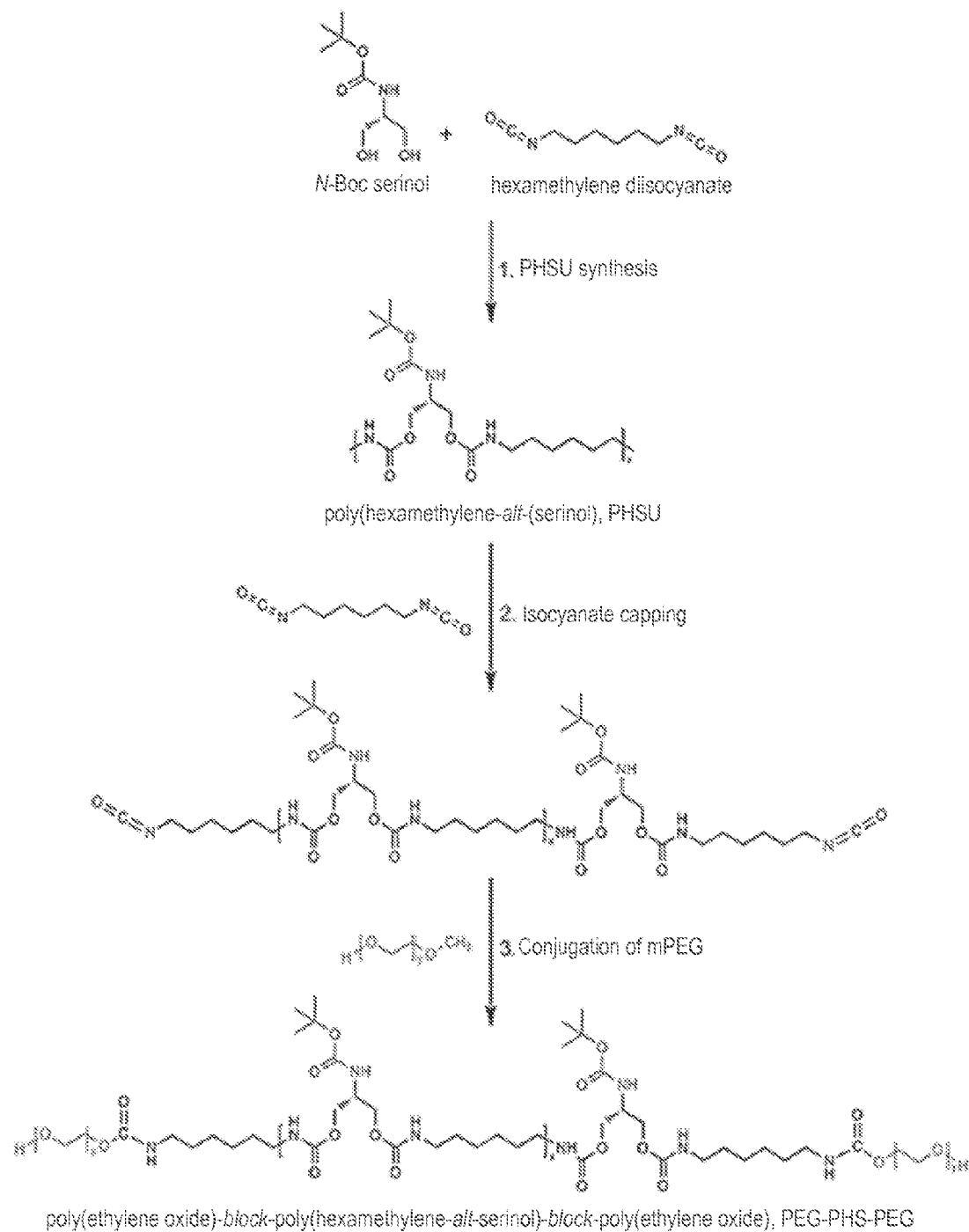
FIG. 2 illustrates a method of forming a triblock polymer: poly(ethylene oxide)-block-poly(hexamethylene-alt-serinol)-block-poly(ethylene oxide) (PEG-PHS-PEG) in accordance with exemplary embodiments of the disclosure.
Figure 17:
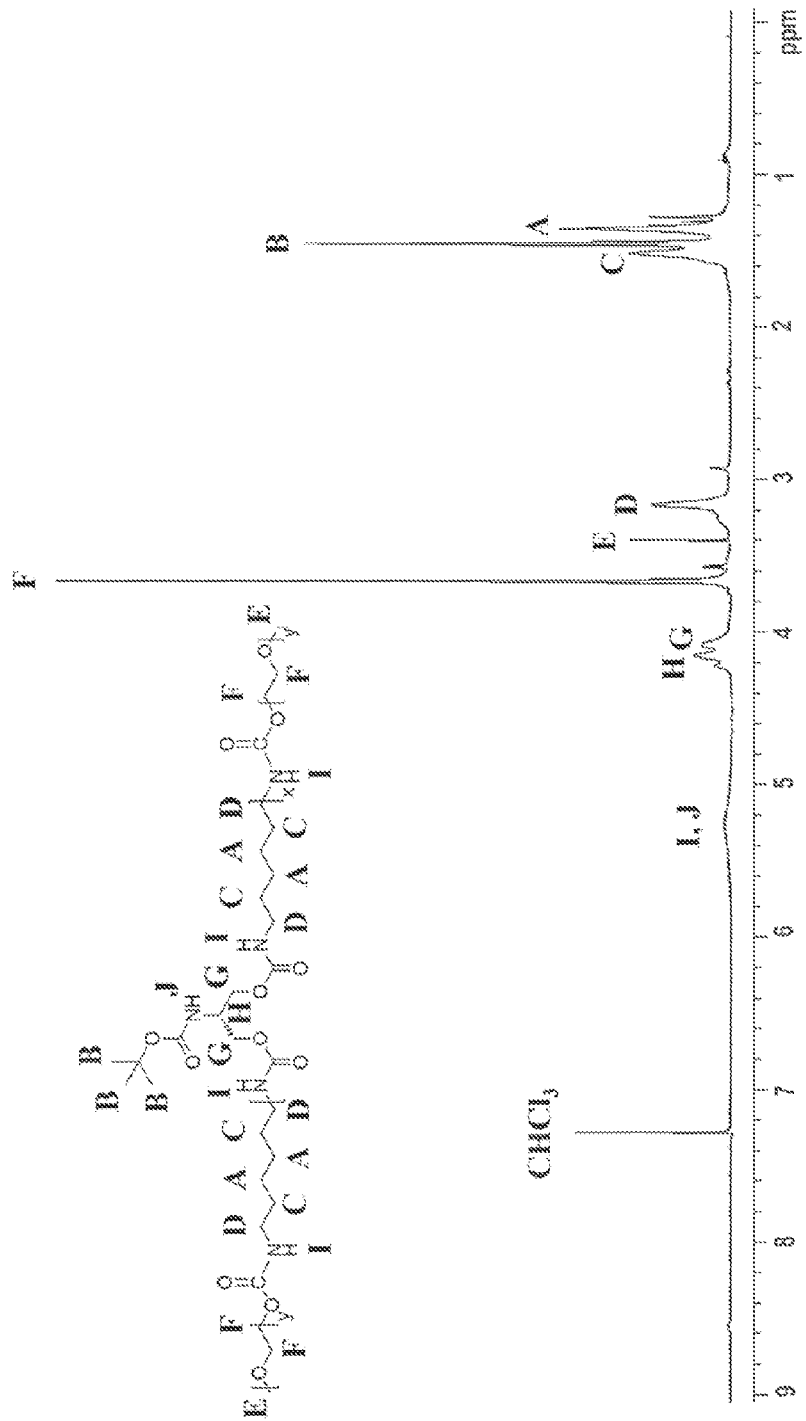
FIG. 17 illustrates a 1H NMR characterization of the PEG-PHS-PEG copolymer.

Synthesis of exemplary micelle compounds can be carried out as a two-step process, wherein PHS is first synthesized at high molecular weight with terminal isocyanates at each end and then reacted with methoxy PEG (mPEG) to produce the triblock copolymer. The triblock polymer, poly(ethylene oxide)-block-poly(hexamethylene-alt-serinol)-block-poly (ethylene oxide), is shown above and an exemplary method of forming PEG-PHS-PEG is illustrated in FIG. 2. FIG. 17 illustrates a 1H NMR characterization of the PEG-PHS-PEG copolymer. The molecular weight of the central PHS block was readily controlled and had a significant impact on the release rate of therapeutic agents from micelles fabricated from these polymers. Exemplary polymers that resulted in micelles with desired release kinetics had the following properties: Mn: 25.3 kDa, Mw: 48.2 kDa, polydispersity index (PI): 1.91.

Synthesis of PHS Block

The PHS polymerization is carried out in a solid-state reaction (i.e., without any solvent) to rapidly produce high molecular weights. N-Boc serinol is weighed out in a RBF and lyophilized for 12 hours at −45° C. and 0.045 mbar. The RBF is then sealed under a nitrogen atmosphere and heated to 85° C. under gentle stirring until all of the NBS has melted. At this point, an equal molar amount of HDI is added drop-wise directly into the reaction and the flask is quickly re-sealed. The reaction is carried out for 5 hours, at which point the polymer is dissolved in a small volume of anhydrous DMF and a 2 molar excess of HDI is added. After 24 hours, the product is precipitated twice is diethyl ether and dried.

Conjugation of mPEG

The dried product is immediately re-dissolved in a small volume of anhydrous DMF in a RBF under gentle stirring, sealed under a nitrogen atmosphere and heated to 70° C. A 10 molar excess of mPEG (MW: 550, Sigma-Aldrich) is lyophilized for one hour at −45° C. and 0.045 mbar and then added to the reaction flask. The PEGylation reaction is carried out for 12 hours. Purification is carried out by three precipitations in diethyl ether and then dried completely by extended rotary evaporation at 50° C. and 10 mbar.

Fabrication of polymeric micelles is typically carried out by one of three methods: direct dialysis, emulsification or extrusion. In direct dialysis, the polymer and drug are dissolved in a suitable solvent (e.g., DMSO) and then loaded into a pre-swollen dialysis membrane submerged in an excess volume of dH2O. In the initial phases of the process, water rapidly swells into the membrane forcing the DMSO, polymer and drug into an emulsion. Eventually, an equilibrium will be reached and a stable emulsion will be achieved. With continued dialysis, DMSO will elute out into the water and polymeric micelles will be left behind, contained within the dialysis membrane. Using this method, full removal of DMSO is very challenging and can take more than 48 hours to achieve.

Figures 18, 19:
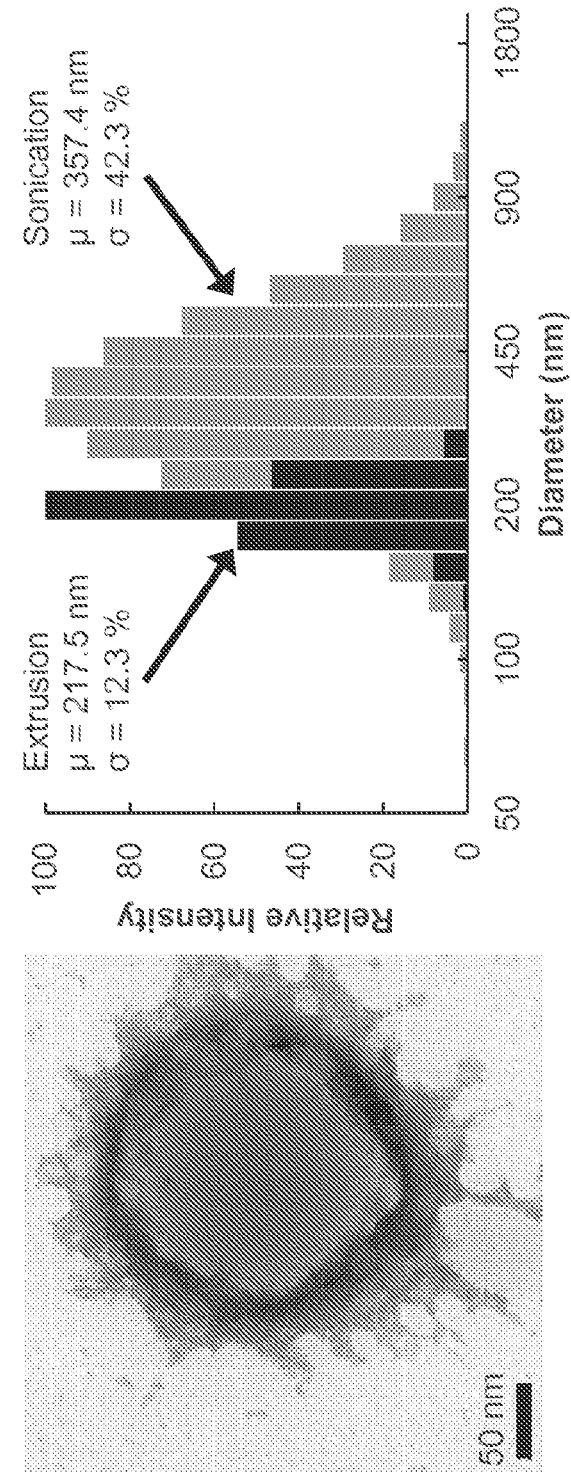
FIG. 18 illustrates a TEM image of a micelle produced by emulsification.
FIG. 19 illustrates dispersion of PEG-PHS-PEG micelles produced by an extrusion technique and by an emulsification technique.

The emulsification method follows the typical fabrication process for polymeric nanoparticles. The polymer and drug are dissolved in a suitable solvent (e.g., DMSO) and then added drop-wise to a volume of water under low-power sonication. As the polymer solution is added to the water, an emulsion is formed and the external energy imparted by sonication forms it into a microemulsion, yielding micelles in the nanometer to micrometer scale. Due to the low log P of triamcinolone acetonide, the drug preferentially partitions into the DMSO phase of the emulsion, yielding high loading efficiencies. After some period of time, DMSO is removed from the system by a series of centrifugations and re-dispersions in water, yielding polymer micelles encapsulating the drug. FIG. 18 illustrates a TEM image of a micelle produced by this method.

For the extrusion method, the polymer and drug are dissolved in DMSO and then added to a larger volume of water to form an emulsion, typically in a 1:20 ratio of DMSO to water. In an extrusion apparatus, the emulsion is passed repeatedly through a filter (e.g., about 50 nm to about 400 nm or about 100 nm average pore size silver filter) by drawing back and forth between two syringes. (Silver was chosen as a suitable filter material for its resistance to DMSO, ability to be sterilized and experimental finding that it consistently yielded the most mono-disperse micelle diameters.) This repeated extrusion through the small pores breaks the emulsion into a microemulsion, achieving the same purpose as the sonication energy in the emulsification procedure. After a number of passes (e.g., 11), the emulsion is removed and DMSO is driven out by a series of centrifugations and re-dispersions in water. A benefit to this procedure is that by virtue of the small filter pore size (<0.2 μm) and by ending the extrusion on the opposite side of the filter that it was begun, the formulation is sterilized during this procedure. Exemplary micelles produced by the extrusion method had a mean diameter of 217.5 nm with a relative standard deviation (RSD) of 12.3%. This result indicated a significantly more monodisperse population of micelles as compared to those produced by the emulsification/sonication method, which were found to have a mean diameter of 357.4 nm with a 42.3% RSD (see FIG. 19).

A potential concern with this extrusion method may be the use of DMSO, which has been shown to be toxic to ocular tissues even at low doses. In order to address this concern, the residual levels of DMSO in fabricated micelles were quantified as a function of purification step. After three iterations of purification, the level of DMSO in the final system was 0.303±0.260% by mass and after five iterations this value dropped further to 0.137±0.0300%. This finding confirms that the current purification process sufficiently removes DMSO and results in a system with DMSO levels 3-fold lower than those reported to be problematic.

Exemplary drug-loaded micelles can be fabricated using any of the techniques described above. By way of example, an extrusion process is used to encapsulate triamcinolone acetonide (TA). In this case, PHS and micronized triamcinolone acetonide are dissolved in DMSO at 2.5 and 0.25 wt % respectively (polymer/DMSO and drug/DMSO). This solution is then added to purified water (milliQ or equivalent) at a 1:20 phase ratio (typically 50 μL polymer/drug solution in 1 mL DMSO) and loaded into one of the glass syringes supplied with the extrusion apparatus (Avestin, Inc., Ottowa, ON). A silver filter (100 nm average pore size, Sterilitech Corp., Kent, Wash.) is placed in the filter holder unit along with several filter support membranes on either side. The emulsion is passed through the filter 11 times and then transferred to a centrifuge tube. Removal of DMSO is carried out by centrifugation at 4500 rcf for 5 minutes, pouring off the supernatant and then re-suspending the micelles in purified water. This DMSO extraction procedure is carried out 3 times. The resulting micelles can either used immediately or lyophilized at −45° C. and 0.045 mbar to produce a dry product.

Cytotoxicities of both HO-PNIPAAm-COOH based RTG and PEG-PHS-PEG polymers described herein were assessed against the ARPE-19 human retinal pigmented epithelial cell line per ISO 10993-5 guidelines using an MTT assay to assess metabolic activity. These results, shown in FIGS. 20-23, showed no statistically significant decrease at any time point for either PHSU-NIPAAm exposed cells ($p<0.01$) or PEG-PHS-PEG exposed cells ($p<0.0001$) at any concentration of either polymer.

Figures 20, 21:
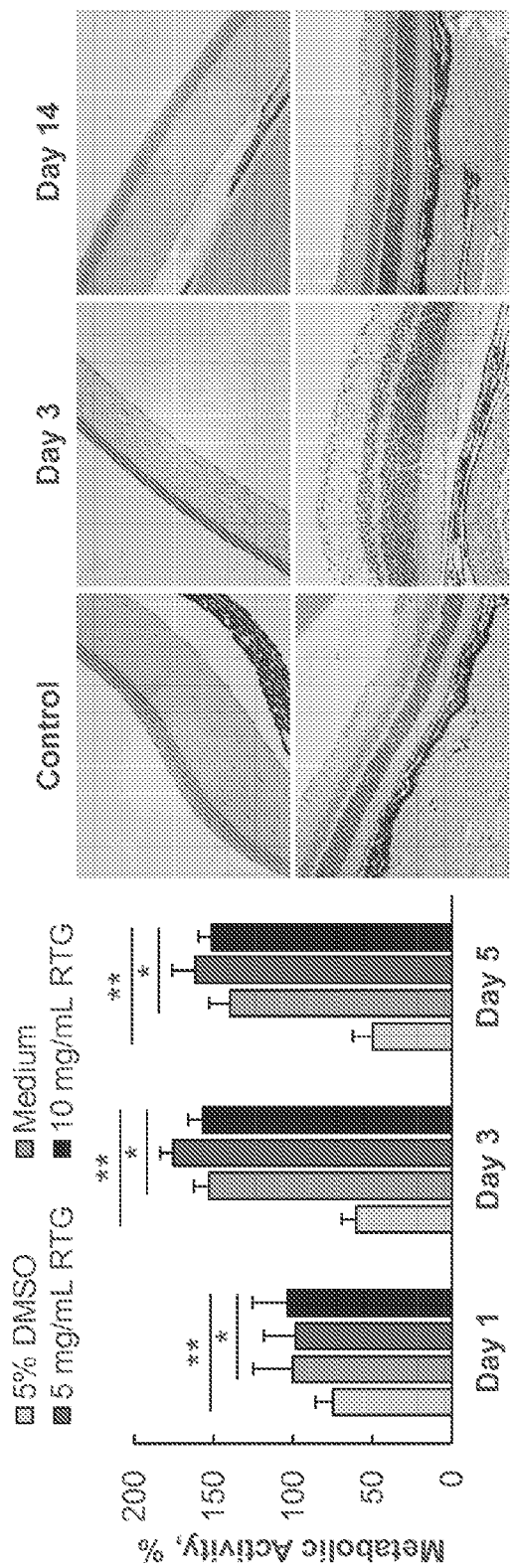
FIGS. 20-23 illustrate cytotoxicities of HO-PNIPAAm-COOH based RTG and PEG-PHS-PEG polymers assessed against an ARPE-19 human retinal pigmented epithelial cell line.
Figures 22, 23:
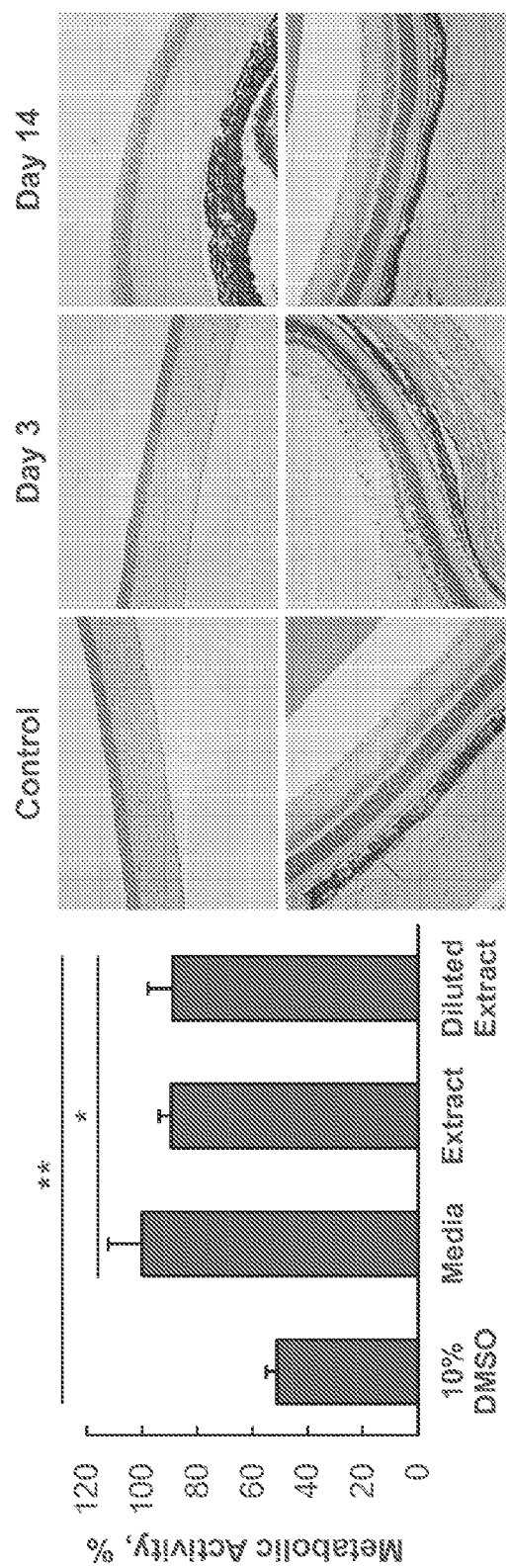

FIG. 20 illustrates that ARPE-19 cells cultured in direct contact with the RTG showed no statistically significant decrease in metabolic activity compared to those grown in pure culture medium ($p>0.2$) at any time point, as measured by MTT assay. Only cells cultured in 5% DMSO showed a statistically significant difference from the pure culture medium samples ($p<0.01$). Data are normalized to the Day 1 medium-only sample and means and standard deviations are plotted for n=5 samples. FIG. 21 illustrates histological sections of cornea (top row) and retina (bottom row) after injection of RTG or PBS (control, left column) were all clear of indications of an inflammatory response. FIG. 22 illustrates that ARPE-19 cells cultured in medium extracted with the PEG-PHS-PEG copolymer showed no statistically significant decrease in metabolic activity compared to those grown in pure culture medium ($p>0.2$), as measured by MTT assay. Only cells cultured in 10% DMSO showed a statistically significant difference from the pure culture medium samples ($p<0.001$). Data are normalized to the pure medium sample and means and standard deviations are plotted for n=5 samples. FIG. 23 illustrates histological sections of cornea (top row) and retina (bottom row) after injection of micelles or PBS (control, left column) were all clear of indications of an inflammatory response.

As shown in FIG. 21 and FIG. 23, representative histological sections of both cornea and retina were clear of infiltrating cells or any indications of an inflammatory response, such as foreign-body giant cells or mast cells. Significant macrophage infiltrations was also absent from all sections. Animals examined during the experimental time course did not display indications of any adverse reactions such as excessive blinking, inflammation, hyperemia or lens or corneal opacity, as would be indicative of a uveitic response.

Degradation

A stumbling block in the application of PNIPAAm-based and other RTGs in biomedical applications has been the difficulty of PNIPAAm (or other molecules/segments) to be cleared by physiological degradation and clearance mechanisms. Efforts to produce biodegradable PNIPAAm-based polymer systems have employed various strategies. Many groups conjugated PNIPAAm homopolymers to biodegradable segments in an effort to degrade the formed thermal gel. While these systems may exhibit molecular weight loss, degradation of the cleavable segments would leave PNIPAAm homopolymers behind, which, can remain insoluble and would likely not be cleared from the site of injection. In order to permit complete biodegradation and clearance of the system, groups have designed specific degradation pathways that result in a significant change in LCST. Specifically, this is generally achieved by cleavage of hydrophobic side chains of monomers co-polymerized with NIPAAm. The degraded polymer—being less hydrophobic—will then exhibit a higher LCST and—if this LCST is above body temperature—will be solubilized and cleared from the system. However, that such systems rely on side chain hydrophobicity to control the LCST results in a relatively inflexible system. For example, conjugation of peptides or targeting antibodies to the polymer backbone—as is highly desirable for tissue engineering applications—would not be possible with such chemistries due to the hydrophilicity contributed by these molecules. In addition, addition of those hydrophobic side chains were reported to significantly increase viscosity of those systems, which may limit their ability to be administered by small-gauge needle injection.

Figure 28:
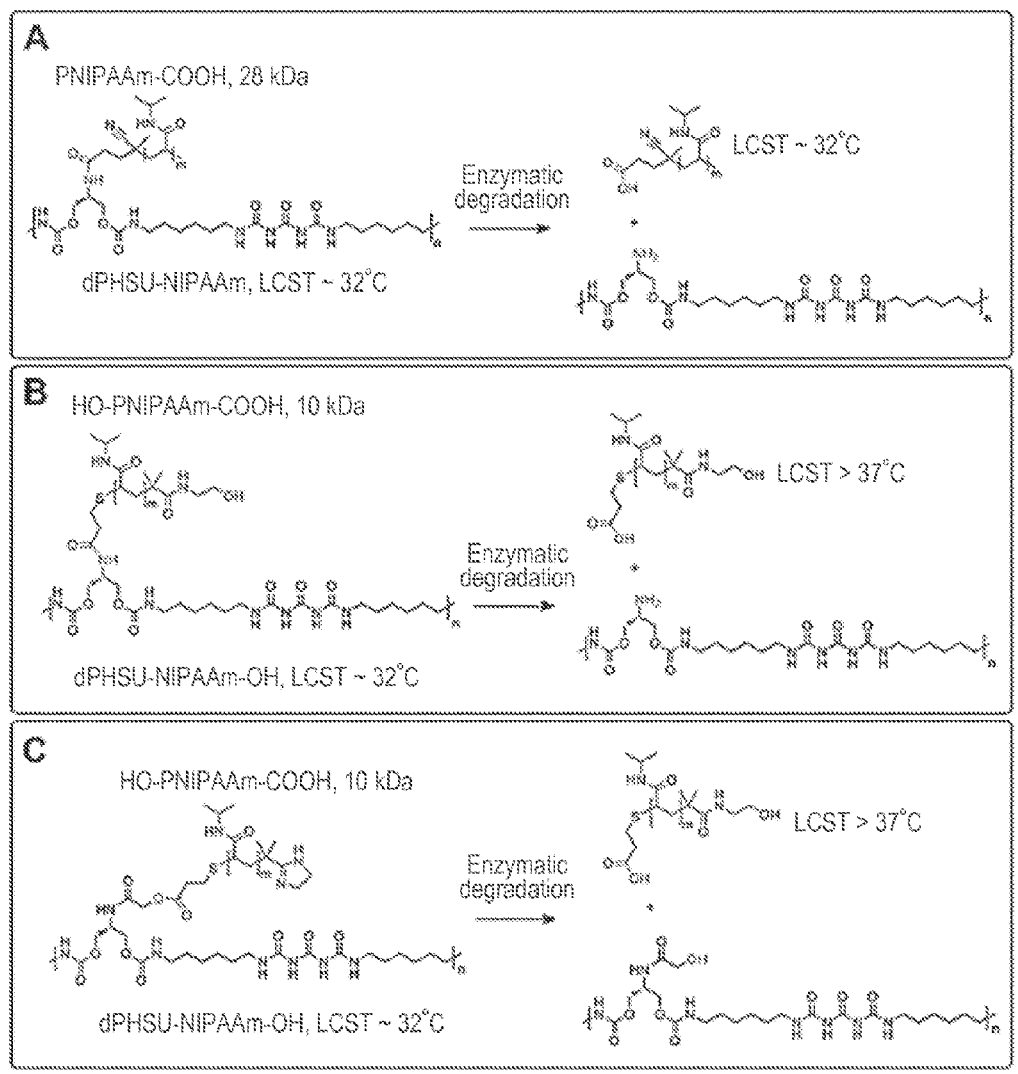
FIG. 28 illustrates a degradation mechanism of HO-PNIPAAm-COOH.

Exemplary copolymers (e.g., PNIPAAm-based) based on LCST modulation before and after polymer degradation as described herein overcome these limitations. FIG. 28 illustrates an exemplary copolymer degradation mechanism in accordance with exemplary embodiments of the disclosure. The degradation can be hydrolytic, enzymatic, or other degradation mechanism. And, although illustrated with a particular copolymer, other copolymers as described herein can be configured to similarly form cleavable and soluble segments/molecules.

Figure 24:
FIG. 24 illustrates accelerated degradation of PNIPAAm-COOH-containing RTG (circles) and HO-PNIPAAm-COOH-containing RTG (squares).
Figure 25:
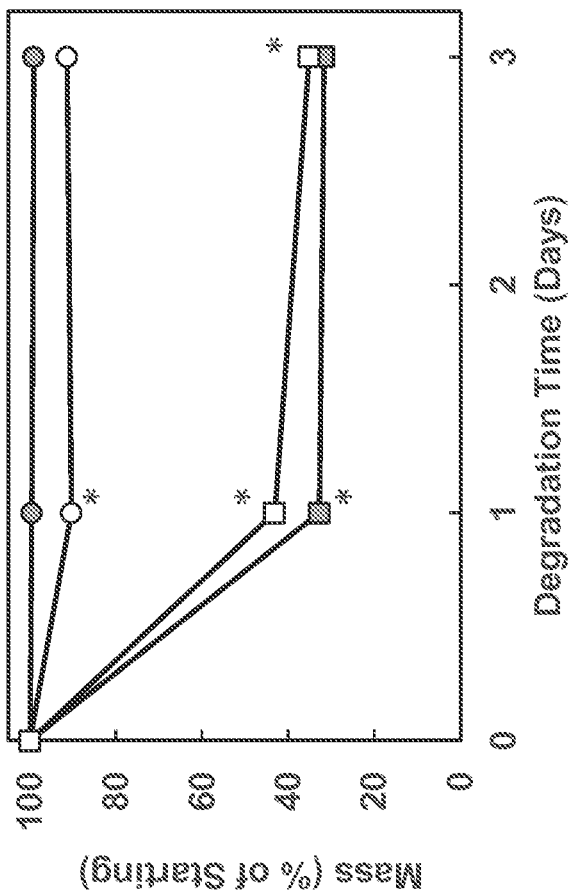
FIG. 25 illustrates accelerated degradation of PNIPAAm-COOH-containing RTG (left vial), HO-PNIPAAm-COOH exposed to HCl (center vial) and HO-PNIPAAm-COOH exposed to papain (right vial).

In order to validate the degradability of this new chemistry, it was subjected to accelerated in vitro degradation testing in both acid (e.g., HCl)-(filled circle or square) and enzyme (e.g., papain)-(open circle or square) catalyzed conditions. In order to isolate the effect of the hydrophilic heterobifunctional PNIPAAm (with LCST above 37° C.), the RTG was also synthesized with a PNIPAAm-COOH (LCST ~32° C.) and degradation of the two systems was compared head-to-head. As shown in FIG. 24 and FIG. 25, PHSU-NIPAAm gels containing a PNIPAAm-COOH chemistry (circles) showed no statistically significant mass loss over 3 days of incubation in either medium ($p>0.2$). In contrast, gels containing the HO-PNIPAAm-COOH chemistry (squares) showed significant mass loss over the first day of incubation ($p<0.0001$) and the enzyme-incubated sample showed continued mass loss between days 1 and 3 ($p<0.05$). Asterisks indicate a statistically significant difference from the previous time point ($p<0.05$). FIG. 25 illustrates that after 3 days under accelerated degradation conditions, the PNIPAAm-COOH-containing RTG (left vial) showed little mass clearance, while RTGs with the HO-PNIPAAm-COOH exposed to HCl (center vial) and papain (right vial) clearly showed a loss of material.

Because the RTG containing the HO-PNIPAAm-COOH based RTG showed mass loss at the first time point, it can be inferred that the amide bonds between the backbone polymer and PNIPAAm were cleaved within this time. As both systems employed the same conjugation chemistry between the backbone and PNIPAAm, it can further be inferred that PNIPAAm was cleaved from the backbone polymer in both gel chemistries. However, since only gels with the high-LCST PNIPAAm chemistry showed mass in these examples, it can be surmised that PNIPAAm in these samples is being resolubilized after cleavage, permitting its clearance from the gel, whereas this is not the case when a PNIPAAm-COOH chemistry is employed.

In Vitro Release Kinetics of HO-PNIPAAm-COOH Based RTG with Micelle Structures As noted above, previous RTG-based drug delivery systems have suffered primarily from their inability to sustain drug release for extended periods of time, which severely limits their clinical utility. The systems described herein, including encapsulated drug-containing polymeric micelles within an RTG system—overcome this limitation in order to realize the full clinical potential of RTG-based drug delivery systems.

Figure 26:
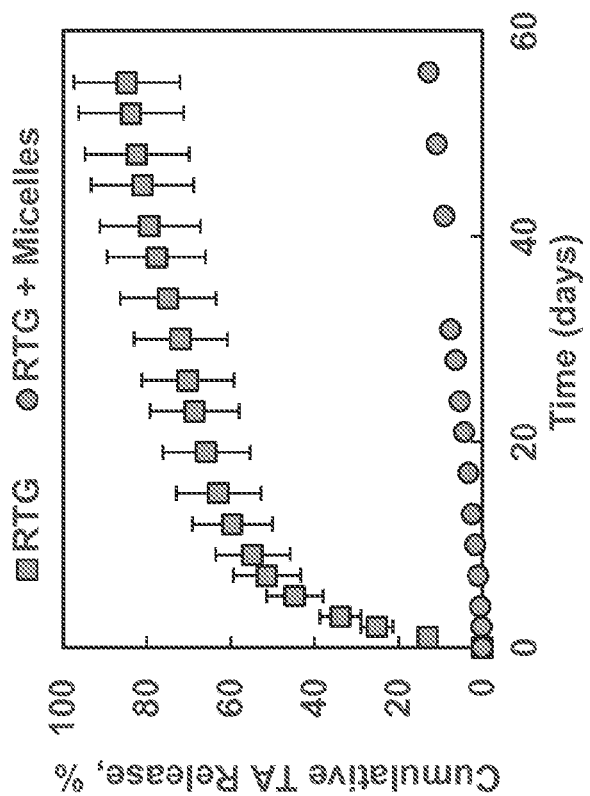
FIG. 26 illustrates release of a therapeutic agent (TA) from the RTG alone (n-=5) and RTG loaded with micelles (n=3).

To assess the drug release behaviors of the RTG, micelles and combined RTG-micelle system, the system components were independently characterized through in vitro release testing using the corticosteroid TA as a model poorly-soluble drug. TA release from the combined RTG-micelle was significantly slower than the RTG alone (FIG. 26), indicating that the beneficial effect of micelle encapsulation was as expected. Within 60 days, the RTG alone released 84.7% of its total TA load, indicating it had neared the end of its therapeutic time frame. However, within the same period, the combined RTG-micelle system had released only 12.8% of its drug load, indicating significant time remaining in its therapeutic utility. As a result, this system would stand to significantly reduce the frequency of administration over the RTG (or especially over a free drug).

Figure 8:
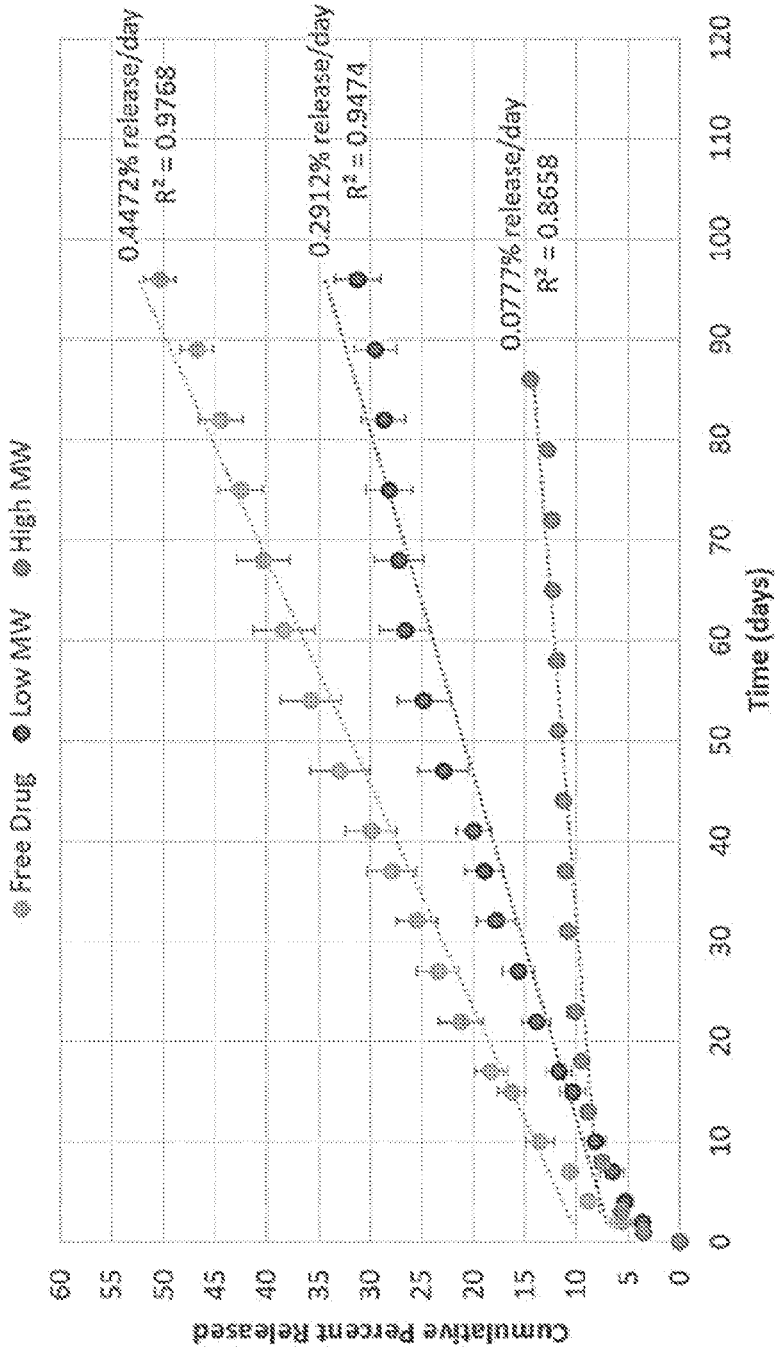
FIG. 8 illustrates release of triamcinolone acetonide from micelles in accordance with exemplary embodiments of the disclosure.
Figure 27:
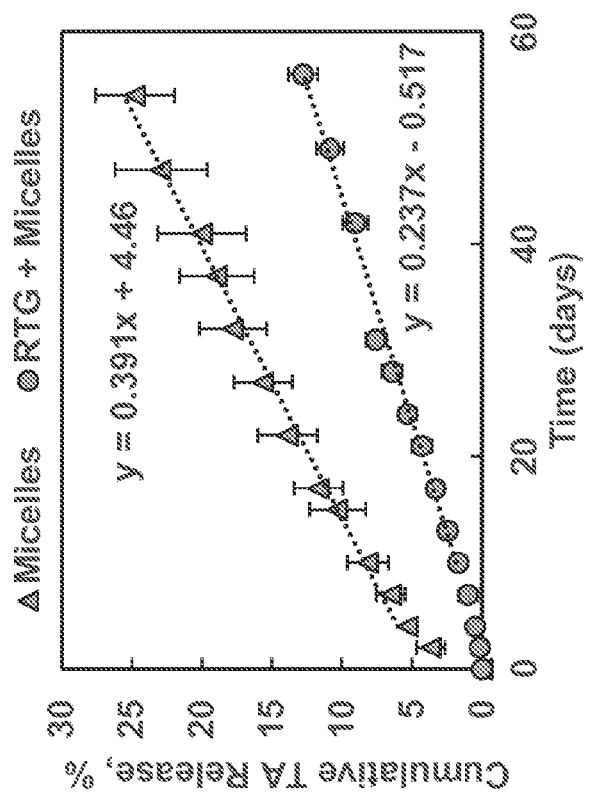
FIG. 27 illustrates release of a therapeutic agent (TA) from TA-loaded micelles on their own (n=3 samples) and TA-micelles encapsulation in the RTG.

In order to understand the impact of encapsulation within the RTG on micelle release properties, release kinetics of TA from micelles alone and those encapsulated within the RTG were also compared directly (FIG. 27). Release of TA from the micelles alone was characterized by two distinct phases. The first phase—a mild burst of drug release—occurred over the first 4 days and accounted for 5.3% of drug release. After 4 days, the second phase of release behavior was established with a release rate of 0.391%/day (or 6.45 μg TA/day per 16.5 mg of micelles). FIG. 8 illustrates release of triamcinolone acetonide (10 wt % loading) from micelles of different molecular weight PEG-PHS-PEG block copolymers.

The RTG-micelle system exhibited a two-phase release behavior. The first phase was characterized by an increasing release rate over the first 6 days. The second phase, which was established by day 8, established a TA release rate of 0.237%/day, which was 40% slower than that of the micelles alone. This slower release may be caused by physical confinement of the micelles within the RTG matrix. PEG-PHS-PEG micelles incubated for 2 weeks were found by SEM to have swollen to nearly 300% their original diameter. This effect would be expected to moderately increase the drug release rate as water enters the micelle core allowing TA to more readily partition out. However, micelles encapsulated within the RTG may have less potential to swell as they are physically confined within a dense polymer matrix, thereby reducing their observed drug release rate.

The initial phase of drug release from the RTG-micelle system, which occurred over the first 6 days, was nearly the inverse of the micelles alone. The micelles exhibited a typical burst release characterized by a high initial release rate that decreased with time to finally reach a steady state. In contrast, the RTG-micelle system exhibited no initial burst release. Instead, the release rate steadily increased over the first several days before finally achieving a steady state. This effect is thought to be caused by the ability of the RTG matrix to "absorb" a quantity of TA as it is released from the micelles. In the beginning of the incubation period, all of the TA is encapsulated within the micelle and the RTG is free of drug. During the first several days, as TA is released from the micelles, the RTG matrix first absorbs the majority of this drug load until it reaches a saturation level, at which point further drug released from the micelles can displace drug within the RTG matrix, which can then partition into the surrounding medium. Because this process would be expected to happen gradually, the first several days of release from the RTG-micelle system are characterized by an increasing drug release rate. This effect results in a dampening of the burst release characteristic of nano-carrier systems and may also be useful in other applications where this initial burst is detrimental to the therapeutic course.

Clinically, the system described above represents a major improvement over the current administration paradigm for TA, which involves high dose intravitreal injections of TA suspensions. These high-dose suspension injections are intended to allow formation of an intravitreal depot of TA, which can provide long-term therapeutic benefit. However, this administration paradigm also has several drawbacks including: a) a high incidence of potentially serious side effects such as elevated intraocular pressure, endophthalmitis, cataract and retinal detachment; and b) transient obstructions in the visual fields of patients due to the opaque nature of the suspension, which can last as long as several days. Injection of the RTG-micelle system, for example to a periocular target, would mitigate these drawbacks due to its lack of burst release behavior and sustained TA release capability.

In accordance with additional embodiments of the disclosure, a system includes a copolymer that includes hydrophobic and hydrophilic blocks. Exemplary copolymers include triblock copolymers (ABA) diblock copolymers (AB) and graft copolymers where A or the graft polymer represents/is a hydrophilic polymer block and B or the backbone polymer represents/is a hydrophobic polymer block.

Exemplary Triblock Copolymers Include:
polyethylene glycol—polyurethane—polyethylene glycol, and
polyethylene glycol—polyamide—polyethylene glycol.

Exemplary Diblock Copolymers Include:
polyethylene glycol—polyurethane, and
polyethylene glycol—polyamide.

Alternatively, the polyethylene glycol blocks could be replaced with polyNIPAAm. The disclosure is not limited to these specific copolymers.

In one specific embodiment, the system is formulated to form micelles slightly below body temperature and be physically mixed with a therapeutic agent, such as an anti-VEGF agent, which is indicated for use in patients with wet age-related macular degeneration. Using a ~30-gauge needle, the system can be injected into the vitreous humor of a patient through a minimally invasive approach 3.5-4 mm behind the limbus. Upon injection, the temperature of the system will rise to body temperature, triggering its physical transformation from a liquid to micelles. The anti-VEGF agent molecules will be incorporated at the center of the micelles, protecting them from the surrounding environment (i.e., improving their long-term stability) and controlling their release. This system will reside in the vitreous humour in micelles, the size of which is small enough so as not to disrupt the light path and cause visual abnormalities. This system can then controllably release the anti-VEGF agent into the vitreous humour for up to a few months or longer, extending its therapeutic lifetime. As the system is biodegradable, it will controllably degrade over many months, allowing for repeat administration without building up a depot of polymer at the injection site.

Each copolymer described herein, including the RTG and micelle forming polymers, may be present in an amount of about 5 wt % to about 40 wt % of the system, and each block may have a molecular weight in the range of about 3500 to about 25,000, or about 500 to about 1000 (hydrophilic blocks), or about 3000 to about 20,000 (hydrophobic blocks). In the case of RTG systems, the system can be gelled from solution state by temperature changes. Therefore, the system can load therapeutics regardless of solubility. However, the system may include water—e.g., at least about 40 wt % water. By way of specific examples having at least 40 wt % water, an amount of the therapeutic may be as follows.

In 5 wt % polymer solution→up to 55 wt % therapeutic agent.

In 10 wt % polymer solution→up to 50 wt % therapeutic agent.

In 40 wt % solution→up to 20 wt % therapeutic agent.

In accordance with various embodiments, the system includes a copolymer and an additional compound (e.g., a polymeric nanoparticle, micelle compound, liposome or a combination thereof) to further facilitate controlled release of the therapeutic agent over a period of time (e.g., 3-12, 3-6, or 4-6 months).

This block copolymer system also lends itself well to conjugation due to the presence of hydroxyl functional groups along its backbone. The groups are used for functionalization of various biomolecules (antibodies for targeting, growth factors, etc.) or drug molecules directly onto the polymer backbone. These functionalized groups will be cleaved hydrolytically upon implantation, providing an additional mechanism for drug or biomolecule delivery.

While these systems are likely best-suited for large molecule therapeutics (cytokines, growth factors, peptides, proteins), they may also readily accept many numerous molecules as well.

Figure 3:
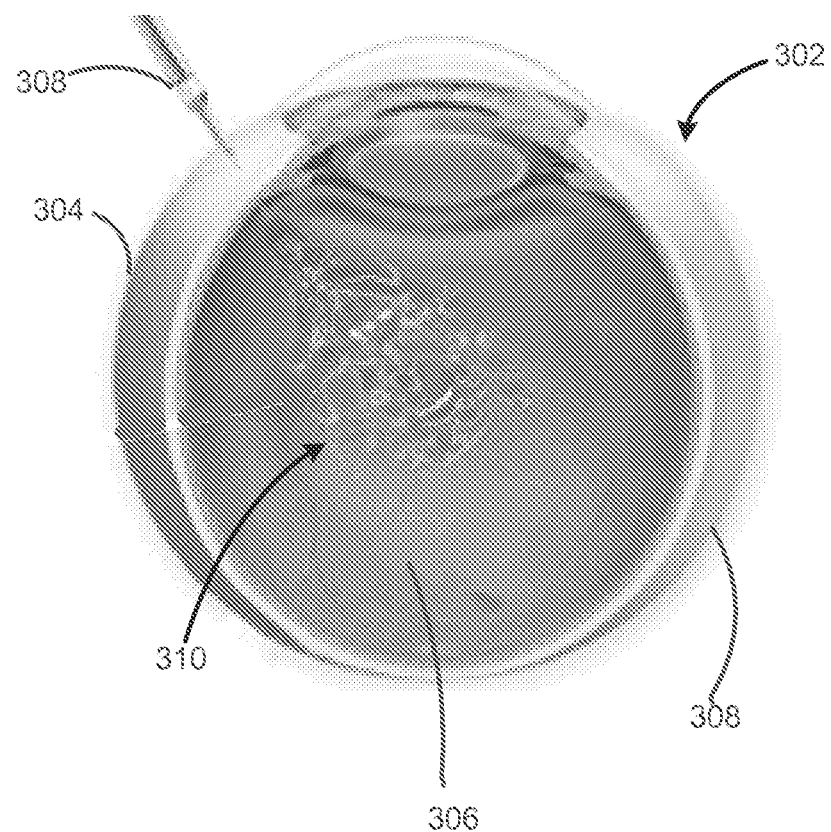
FIG. 3 illustrates a method of using a system in accordance with exemplary embodiments of the disclosure.

Turning now to FIG. 3, a method of injecting a system, as described herein, is illustrated. FIG. 3 illustrates that the system can be injected (e.g., using a-syringe 308) into an eye 302 through, e.g., a sclera 304 of eye 302 and into a vitreous humor region 306. Once injected, the system rapidly forms a gel 310 within vitreous humor region 306 of the eye 302.

Figure 4:
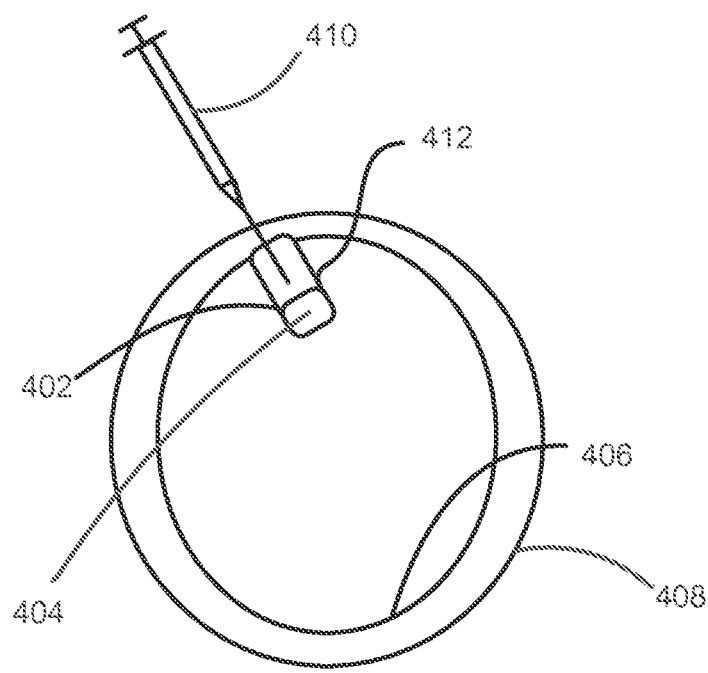
FIG. 4 illustrates a device and a method of using a system in accordance with additional exemplary embodiments of the disclosure.

FIG. 4 illustrates a device 402, including a system 404 as described herein and a method of treating an eye by injecting system 404 into device 402. Device 402 includes a reservoir 412 and may be implanted in vivo—e.g., anchored to a sclera 406 within an eye 408. System 404 may be injected into reservoir 412 of device 404 using, e.g., syringe 410. As noted above, device 402 may include a secondary mechanism to further control of elution of the system. For example, the device may include nanopores or other means for limiting diffusion of the systems described herein.

The present disclosure has been described above with reference to a number of exemplary embodiments and examples. It should be appreciated that the particular embodiments shown and described herein are illustrative of the preferred embodiments of the disclosure and its best mode, and are not intended to limit the scope of the disclosure as set forth in the claims. It will be recognized that changes and modifications may be made to the embodiments described herein without departing from the scope of the present disclosure. These and other changes or modifications are intended to be included within the scope of the present disclosure, as expressed in the following claims and the legal equivalents thereof.

The disclosure claimed is:

1. A therapeutic agent delivery system, the system comprising:
    a copolymer with reverse thermal gelling properties, the copolymer having thermally-sensitive molecules, hydrophobic segments and hydrophilic segments, or a combination thereof;
    a compound selected the from the group consisting of one or more nanoparticles, micelles, liposome systems, or a combination thereof, the compound distributed within the reverse thermal gel composition; and
    a first therapeutic agent at least partially encapsulated in or bound to the compound,
    wherein the copolymer comprises a grafted copolymer, wherein a backbone polymer comprises poly[hexamethylene-alt-(serinol; urea)] (PHSU), and a graft polymer that is selected from the group consisting of poly(N-isopropylacrylamide) (PNIPAAm), hydroxypropylcellulose, poly(vinylcaprolactame), polyethylene oxide, polyvinylmethylether, polyhydroxyethylmethacrylate, poly(N-acryloylglycinamide), ureidofunctionalized polymer, acrylamide-based copolymer, and acrylonitrile-based copolymer compounds,
    wherein the system is configured to provide sustained release of the first therapeutic agent for a period of greater than 3 months, and
    wherein a combination of the copolymer and the compound provides a controlling mechanism for release of the therapeutic agent, allowing for its sustained delivery over an extended period of time.

2. The therapeutic agent delivery system of claim 1, wherein the backbone polymer comprises esterified poly [hexamethylene-alt-(serinol; urea)].

3. The therapeutic agent delivery system of claim 1, wherein the backbone polymer has a molecular weight of about 2000 Da to about 50000 Da.

4. The therapeutic agent delivery system of claim 1, wherein the graft polymer has a molecular weight between about 2000 and 50000.

5. The therapeutic agent delivery system of claim 1, wherein the backbone comprises a diol compound, wherein the diol comprises an amino-substituted or N-substituted serinol in which the N is substituted with one of a hydrogen, a protective group or an active agent.

6. The therapeutic agent delivery system of claim 1, wherein the graft polymer comprises poly(N-isopropylacrylamide).

7. The therapeutic agent delivery system of claim 1, wherein the graft polymer has a molecular weight of about 2000 Da to about 100000 Da.

8. A therapeutic agent delivery system, the system comprising:
    a copolymer comprising a hydrophobic segment and one or more hydrophilic segments that self-assembles into a micelle configuration; and
    a first therapeutic agent at least partially encapsulated in the micelle configuration,
    wherein the hydrophilic segments are derived from polyethylene glycol,
    wherein the hydrophobic segment is derived from poly (hexamethylene-alt-serinol) (PHS), and
    wherein the hydrophobic segment has a molecular weight of about 75,000 to about 200,000 Da.

9. The therapeutic agent delivery system of claim 8, wherein the copolymer is a triblock copolymer, wherein the hydrophobic segment comprises poly(hexamethylene-alt-serinol), and wherein the hydrophilic segment is polyethylene oxide.

10. The therapeutic agent delivery system of claim 8 wherein the hydrophobic segment is synthesized by the reaction of hexamethylene diisocyanate and N-Boc serinol.

11. The therapeutic agent delivery system of claim 8, wherein at least one of the one or more hydrophilic segments is poly(ethylene oxide).

12. The therapeutic agent delivery system of claim 8, wherein at least one of the one or more hydrophilic segments comprises poly(ethylene oxide), wherein the hydrophobic segment comprises poly(hexamethylene-alt-serinol), and wherein the molecular weight of the hydrophilic segment is between about 500 and about 2000 Da.

* * * * *